US010050650B2

(12) United States Patent
O'Hagan et al.

(10) Patent No.: US 10,050,650 B2
(45) Date of Patent: Aug. 14, 2018

(54) METHOD, APPARATUS, AND COMPUTER PROGRAM PRODUCT IMPROVING REGISTRATION WITH REAL TIME LOCATION SERVICES

(71) Applicant: ZIH CORP., Lincolnshire, IL (US)

(72) Inventors: James J. O'Hagan, McHenry, IL (US); Rodrigo G. Alonso, Gilroy, CA (US); Michael A. Wohl, Talbott, TN (US)

(73) Assignee: ZIH Corp., Lincolnshire, IL (US)

( * ) Notice: Subject to any disclaimer, the term of this patent is extended or adjusted under 35 U.S.C. 154(b) by 0 days.

(21) Appl. No.: 15/651,347

(22) Filed: Jul. 17, 2017

(65) Prior Publication Data
US 2017/0317702 A1 Nov. 2, 2017

Related U.S. Application Data

(63) Continuation of application No. 14/298,396, filed on Jun. 6, 2014, now Pat. No. 9,742,450.
(Continued)

(51) Int. Cl.
*H04B 1/10* (2006.01)
*A63B 24/00* (2006.01)
(Continued)

(52) U.S. Cl.
CPC .......... *H04B 1/1036* (2013.01); *A41D 1/002* (2013.01); *A41D 1/04* (2013.01); *A42B 3/30* (2013.01); *A63B 24/0021* (2013.01); *A63B 24/0062* (2013.01); *A63B 71/06* (2013.01); *A63B 71/0619* (2013.01); *A63B 71/0622* (2013.01);
(Continued)

(58) Field of Classification Search
CPC ....... H04W 84/18; H04W 4/02; H04W 64/00; G06F 17/2235; G08C 17/02; G06K 2017/0045
See application file for complete search history.

(56) References Cited

U.S. PATENT DOCUMENTS 3,732,500 A 5/1973 Dishal et al.
4,270,145 A 5/1981 Farina
(Continued)

FOREIGN PATENT DOCUMENTS

EP 1235077 A2 8/2002
EP 1241616 A2 9/2002
(Continued)

OTHER PUBLICATIONS

Marchant, J., "Secure Animal Identification and Source Verification," JM Communications, UK, 2002.
(Continued)

*Primary Examiner* — Liton Miah

(57) ABSTRACT

An example disclosed method for registering an unregistered radio frequency (RF) location tag carried by a participant includes receiving blink data from an unregistered RF location tag; determining a tag location based on the blink data received from the unregistered RF location tag; directing a camera to view the tag location determined based on the blink data received from the unregistered RF location tag; identifying a participant at the tag location using image data obtained by the camera; and registering the unregistered RF location tag with the identified participant.

20 Claims, 10 Drawing Sheets

Related U.S. Application Data

(60) Provisional application No. 61/831,990, filed on Jun. 6, 2013.

(51) Int. Cl.

| | | |
|---|---|---|
| *G06F 17/30* | (2006.01) | |
| *H04L 29/08* | (2006.01) | |
| *A41D 1/00* | (2018.01) | |
| *A41D 1/04* | (2006.01) | |
| *A42B 3/30* | (2006.01) | |
| *A63B 71/06* | (2006.01) | |
| *H04Q 9/00* | (2006.01) | |
| *G06Q 50/22* | (2018.01) | |
| *H04B 1/719* | (2011.01) | |
| *G09B 19/00* | (2006.01) | |
| *H04L 12/26* | (2006.01) | |
| *G06N 5/02* | (2006.01) | |
| *G06F 19/00* | (2018.01) | |
| *G06K 9/00* | (2006.01) | |
| *H04W 4/02* | (2018.01) | |
| *H04B 1/7097* | (2011.01) | |
| *G08C 17/02* | (2006.01) | |
| *G06K 7/10* | (2006.01) | |
| *H04B 1/7163* | (2011.01) | |
| *G06Q 50/20* | (2012.01) | |
| *G16H 50/50* | (2018.01) | |
| *G06K 17/00* | (2006.01) | |
| *G06Q 90/00* | (2006.01) | |

(52) U.S. Cl.
CPC ...... *A63B 71/0686* (2013.01); *G06F 17/3087* (2013.01); *G06F 17/30864* (2013.01); *G06F 17/30876* (2013.01); *G06F 19/3437* (2013.01); *G06K 7/10227* (2013.01); *G06K 7/10297* (2013.01); *G06K 7/10306* (2013.01); *G06K 7/10366* (2013.01); *G06K 9/00342* (2013.01); *G06N 5/02* (2013.01); *G06Q 50/20* (2013.01); *G06Q 50/22* (2013.01); *G08C 17/02* (2013.01); *G09B 19/0038* (2013.01); *G16H 50/50* (2018.01); *H04B 1/7097* (2013.01); *H04B 1/719* (2013.01); *H04B 1/71635* (2013.01); *H04B 1/71637* (2013.01); *H04L 43/04* (2013.01); *H04L 67/12* (2013.01); *H04Q 9/00* (2013.01); *H04W 4/02* (2013.01); *A63B 24/00* (2013.01); *A63B 2024/0025* (2013.01); *A63B 2220/12* (2013.01); *A63B 2220/836* (2013.01); *A63B 2225/50* (2013.01); *A63B 2225/54* (2013.01); *G06K 2017/0045* (2013.01); *G06Q 90/00* (2013.01)

(56) References Cited

U.S. PATENT DOCUMENTS

| | | |
|---|---|---|
| 5,119,104 A | 6/1992 | Heller |
| 5,469,409 A | 11/1995 | Anderson et al. |
| 5,513,854 A | 5/1996 | Daver |
| 5,645,077 A | 7/1997 | Foxlin |
| 5,699,244 A | 12/1997 | Clark, Jr. et al. |
| 5,793,630 A | 8/1998 | Theimer et al. |
| 5,901,172 A | 5/1999 | Fontana et al. |
| 5,920,287 A | 7/1999 | Belcher et al. |
| 5,930,741 A | 7/1999 | Kramer |
| 5,995,046 A | 11/1999 | Belcher et al. |
| 6,028,626 A | 2/2000 | Aviv |
| 6,121,926 A | 9/2000 | Belcher et al. |
| 6,176,837 B1 | 1/2001 | Foxlin |
| 6,204,813 B1 | 3/2001 | Wadell et al. |
| 6,366,242 B1 | 4/2002 | Boyd et al. |
| 6,380,894 B1 | 4/2002 | Boyd et al. |
| 6,593,885 B2 | 7/2003 | Wisherd et al. |
| 6,655,582 B2 | 12/2003 | Wohl et al. |
| 6,710,713 B1 | 3/2004 | Russo |
| 6,812,884 B2 | 11/2004 | Richley et al. |
| 6,836,744 B1 | 12/2004 | Asphahani et al. |
| 6,882,315 B2 | 4/2005 | Richley et al. |
| 7,009,638 B2 | 3/2006 | Gruber et al. |
| 7,190,271 B2 | 3/2007 | Boyd |
| 7,667,604 B2 | 2/2010 | Ebert et al. |
| 7,671,802 B2 | 3/2010 | Walsh et al. |
| 7,710,322 B1 | 5/2010 | Ameti et al. |
| 7,739,076 B1 | 6/2010 | Vock et al. |
| 7,755,541 B2 | 7/2010 | Wisherd et al. |
| 7,899,006 B2 | 3/2011 | Boyd |
| 7,969,348 B2 | 6/2011 | Baker et al. |
| 8,077,981 B2 | 12/2011 | Elangovan et al. |
| 8,269,835 B2 | 9/2012 | Grigsby et al. |
| 8,279,051 B2 | 10/2012 | Khan |
| 8,457,392 B2 | 6/2013 | Cavallaro et al. |
| 8,568,278 B2 | 10/2013 | Riley et al. |
| 8,696,458 B2 | 4/2014 | Foxlin et al. |
| 8,705,671 B2 | 4/2014 | Ameti et al. |
| 8,775,916 B2 | 7/2014 | Pulsipher et al. |
| 8,780,204 B2 | 7/2014 | DeAngelis et al. |
| 8,795,045 B2 | 8/2014 | Sorrells et al. |
| 8,842,002 B2 | 9/2014 | Rado |
| 8,989,880 B2 | 3/2015 | Wohl et al. |
| 9,002,485 B2 | 4/2015 | Wohl et al. |
| 9,014,830 B2 | 4/2015 | Wohl et al. |
| 9,081,076 B2 | 7/2015 | DeAngelis et al. |
| 9,381,645 B1 | 7/2016 | Yarlagadda et al. |
| 2001/0010541 A1 | 8/2001 | Fernandez et al. |
| 2001/0030625 A1 | 10/2001 | Doles et al. |
| 2002/0004398 A1 | 1/2002 | Ogino et al. |
| 2002/0041284 A1 | 4/2002 | Konishi et al. |
| 2002/0114493 A1 | 8/2002 | McNitt et al. |
| 2002/0116147 A1 | 8/2002 | Vock et al. |
| 2002/0130835 A1 | 9/2002 | Brosnan |
| 2002/0135479 A1 | 9/2002 | Belcher et al. |
| 2003/0090387 A1 | 5/2003 | Lestienne et al. |
| 2003/0095186 A1 | 5/2003 | Aman et al. |
| 2003/0128100 A1 | 7/2003 | Burkhardt et al. |
| 2003/0163287 A1 | 8/2003 | Vock et al. |
| 2003/0227453 A1 | 12/2003 | Beier et al. |
| 2004/0022227 A1 | 2/2004 | Lynch et al. |
| 2004/0062216 A1 | 4/2004 | Nicholls et al. |
| 2004/0108954 A1 | 6/2004 | Richley et al. |
| 2004/0178960 A1 | 9/2004 | Sun |
| 2004/0249969 A1 | 12/2004 | Price |
| 2004/0260470 A1 | 12/2004 | Rast |
| 2004/0260828 A1 | 12/2004 | Price |
| 2005/0026563 A1 | 2/2005 | Leeper et al. |
| 2005/0031043 A1 | 2/2005 | Paquelet |
| 2005/0059998 A1 | 3/2005 | Norte et al. |
| 2005/0073418 A1 | 4/2005 | Kelliher et al. |
| 2005/0075079 A1 | 4/2005 | Jei et al. |
| 2005/0093976 A1 | 5/2005 | Valleriano et al. |
| 2005/0148281 A1 | 7/2005 | Sanchez-Castro et al. |
| 2005/0207617 A1 | 9/2005 | Samoff |
| 2006/0067324 A1 | 3/2006 | Kim et al. |
| 2006/0139167 A1 | 6/2006 | Davie et al. |
| 2006/0164213 A1 | 7/2006 | Burghard et al. |
| 2006/0252476 A1 | 11/2006 | Bahou |
| 2006/0264730 A1 | 11/2006 | Stivoric et al. |
| 2006/0271912 A1 | 11/2006 | Mickle et al. |
| 2006/0281061 A1 | 12/2006 | Hightower et al. |
| 2007/0091292 A1 | 4/2007 | Cho et al. |
| 2007/0176749 A1 | 8/2007 | Boyd |
| 2007/0296723 A1 | 12/2007 | Williams |
| 2008/0065684 A1 | 3/2008 | Zilberman |
| 2008/0106381 A1 | 5/2008 | Adamec et al. |
| 2008/0113787 A1 | 5/2008 | Alderucci et al. |
| 2008/0129825 A1 | 6/2008 | DeAngelis et al. |
| 2008/0140233 A1 | 6/2008 | Seacat |
| 2008/0186231 A1 | 8/2008 | Aljadeff et al. |
| 2008/0204248 A1 | 8/2008 | Cam Winget et al. |
| 2008/0262885 A1 | 10/2008 | Jain et al. |
| 2008/0266131 A1 | 10/2008 | Richardson et al. |

(56) References Cited

U.S. PATENT DOCUMENTS

| | | |
|---|---|---|
| 2008/0269016 A1 | 10/2008 | Ungari et al. |
| 2008/0281443 A1 | 11/2008 | Rodgers |
| 2008/0285805 A1 | 11/2008 | Luinge et al. |
| 2008/0291024 A1 | 11/2008 | Zhang et al. |
| 2009/0210078 A1 | 8/2009 | Crowley |
| 2009/0231198 A1 | 9/2009 | Walsh et al. |
| 2010/0026809 A1 | 2/2010 | Curry |
| 2010/0045508 A1 | 2/2010 | Ekbal et al. |
| 2010/0054304 A1 | 3/2010 | Barnes et al. |
| 2010/0060452 A1 | 3/2010 | Schuster et al. |
| 2010/0080163 A1 | 4/2010 | Krishnamoorthi et al. |
| 2010/0117837 A1 | 5/2010 | Stirling et al. |
| 2010/0150117 A1 | 6/2010 | Aweya et al. |
| 2010/0250305 A1 | 9/2010 | Lee et al. |
| 2010/0278386 A1 | 11/2010 | Hoeflinger |
| 2010/0283630 A1 | 11/2010 | Alonso |
| 2010/0328073 A1 | 12/2010 | Nikitin et al. |
| 2011/0013087 A1 | 1/2011 | House et al. |
| 2011/0025847 A1 | 2/2011 | Park et al. |
| 2011/0054782 A1 | 3/2011 | Kaahui |
| 2011/0063114 A1 | 3/2011 | Ikoyan |
| 2011/0084806 A1 | 4/2011 | Perkins |
| 2011/0134240 A1 | 6/2011 | Anderson et al. |
| 2011/0140970 A1 | 6/2011 | Fukagawa et al. |
| 2011/0169959 A1* | 7/2011 | DeAngelis ......... A63B 24/0021 348/157 |
| 2011/0188513 A1 | 8/2011 | Christoffersson et al. |
| 2011/0261195 A1 | 10/2011 | Martin et al. |
| 2011/0300905 A1 | 12/2011 | Levi |
| 2011/0320322 A1 | 12/2011 | Roslak et al. |
| 2012/0014278 A1 | 1/2012 | Ameti et al. |
| 2012/0015665 A1 | 1/2012 | Farley et al. |
| 2012/0024516 A1 | 2/2012 | Bhadurt et al. |
| 2012/0042326 A1 | 2/2012 | Jain et al. |
| 2012/0057634 A1 | 3/2012 | Shi et al. |
| 2012/0057640 A1 | 3/2012 | Shi et al. |
| 2012/0065483 A1 | 3/2012 | Chung |
| 2012/0081531 A1 | 4/2012 | DeAngelis et al. |
| 2012/0112904 A1 | 5/2012 | Nagy |
| 2012/0126973 A1 | 5/2012 | DeAngelis et al. |
| 2012/0139708 A1 | 6/2012 | Paradiso et al. |
| 2012/0184878 A1 | 7/2012 | Najafi et al. |
| 2012/0212505 A1 | 8/2012 | Burroughs et al. |
| 2012/0218301 A1 | 8/2012 | Miller |
| 2012/0225676 A1 | 9/2012 | Boyd et al. |
| 2012/0246795 A1 | 10/2012 | Scheffler et al. |
| 2012/0256745 A1 | 10/2012 | Piett et al. |
| 2012/0268239 A1 | 10/2012 | Ljung et al. |
| 2013/0003860 A1 | 1/2013 | Sasai et al. |
| 2013/0021142 A1 | 1/2013 | Matsui et al. |
| 2013/0021206 A1 | 1/2013 | Hach et al. |
| 2013/0041590 A1 | 2/2013 | Bunch et al. |
| 2013/0041775 A1 | 2/2013 | Rosenberg |
| 2013/0066448 A1 | 3/2013 | Alonso |
| 2013/0076645 A1 | 3/2013 | Anantha et al. |
| 2013/0096704 A1 | 4/2013 | Case, Jr. |
| 2013/0138386 A1 | 5/2013 | Jain et al. |
| 2013/0138518 A1 | 5/2013 | White et al. |
| 2013/0142384 A1 | 6/2013 | Ofek |
| 2013/0197981 A1 | 8/2013 | Vendetti |
| 2013/0257598 A1 | 10/2013 | Kawaguchi et al. |
| 2013/0268185 A1 | 10/2013 | Rabbath et al. |
| 2013/0339156 A1 | 12/2013 | Sanjay et al. |
| 2014/0038544 A1 | 2/2014 | Jones et al. |
| 2014/0055588 A1 | 2/2014 | Bangera et al. |
| 2014/0062728 A1 | 3/2014 | Soto et al. |
| 2014/0089243 A1 | 3/2014 | Oppenheimer |
| 2014/0145828 A1 | 5/2014 | Bassan-Eskenazi et al. |
| 2014/0156036 A1 | 6/2014 | Huang |
| 2014/0170607 A1 | 6/2014 | Hsiao et al. |
| 2014/0221137 A1 | 8/2014 | Krysiak et al. |
| 2014/0301427 A1 | 10/2014 | Khalaf-Allah |
| 2014/0320660 A1 | 10/2014 | DeAngelis et al. |
| 2014/0347193 A1* | 11/2014 | Ljung ................... H04L 67/04 340/870.01 |
| 2014/0361875 A1 | 12/2014 | O'Hagan et al. |
| 2014/0361906 A1 | 12/2014 | Hughes et al. |
| 2014/0364141 A1 | 12/2014 | O'Hagan et al. |
| 2014/0365415 A1 | 12/2014 | Stelfox et al. |
| 2015/0002272 A1 | 1/2015 | Alonso et al. |
| 2015/0057981 A1 | 2/2015 | Gross |
| 2015/0085111 A1 | 3/2015 | Lavery |
| 2015/0097653 A1 | 4/2015 | Gibbs et al. |
| 2015/0335953 A1 | 11/2015 | Wohl et al. |
| 2015/0355311 A1 | 12/2015 | O'Hagan et al. |
| 2015/0358852 A1 | 12/2015 | Richley et al. |
| 2015/0360133 A1 | 12/2015 | MacCallum et al. |
| 2015/0375041 A1 | 12/2015 | Richley et al. |
| 2015/0375083 A1 | 12/2015 | Stelfox et al. |
| 2015/0379387 A1 | 12/2015 | Richley |
| 2016/0059075 A1 | 3/2016 | Molyneux et al. |
| 2016/0097837 A1 | 4/2016 | Richley et al. |

FOREIGN PATENT DOCUMENTS

| | | |
|---|---|---|
| EP | 1253438 A2 | 10/2002 |
| EP | 1503513 A1 | 2/2005 |
| EP | 2474939 A1 | 11/2012 |
| WO | 1998/005977 A1 | 2/1998 |
| WO | 1999/061936 A1 | 12/1999 |
| WO | 2001/008417 A1 | 2/2001 |
| WO | 2006/022548 A1 | 3/2006 |
| WO | 2010/083943 A1 | 7/2010 |
| WO | 2014/197600 A1 | 12/2014 |
| WO | 2015/051813 A1 | 4/2015 |

OTHER PUBLICATIONS

Gueziec, A., "Tracking Pitches for Broadcast Television," Aug. 7, 2002. <http://baseball.physics.illinois.edu/TrackingBaseballs.pdf>.

"A Guide to Using NLIS Approved Ear Tags and Rumen Boluses", National Livestock Identification Scheme, Meat & Livestock Australia Limited, North Sydney, Australia, May 2003.

Fontana et al., "Commercialization of an Ultra Wideband Precision Asset Location System," 2003 IEEE Conference on Ultra Wideband Systems and Technologies, Nov. 16-19, 2003.

"RFID in the Australian Meat and Livestock Industry", Allflex Australia Pty Ltd., Capalaba, QLD (AU), Data Capture Suppliers Guide, 2003-2004.

CattleLog Pro, eMerge Interactive, Inc., Sebastian, FL, 2004.

Zhu et al., "A Real-Time Articulated Human Motion Tracking Using Tri-Axis Inertial/Magnetic Sensors Package," IEEE Transactions on Neural Systems and Rehabilitation Engineering, vol. 12, No. 2. Jun. 2004, pp. 295-302.

Cheong et al., "Synchronization, TOA and Position Estimation for Low-Complexity LDR UWB Devices", Ultra-Wideband, 2005 IEEE International Conference, Zurich, Switzerland, Sep. 5-8, 2005, Piscataway, NJ, USA, IEEE, pp. 480-484.

King, "NAIS Cattle ID Pilot Projects Not Needed, Since Proven Advanced Technology Already Exists," Scoring System, Inc., Sarasota, FL, Dec. 27, 2005. <www.prweb.com/releases/2005/12prweb325888.htm>.

Zhang et al., "UWB Systems for Wireless Sensor Networks", Proceedings of the IEEE, IEEE. New York, US, vol. 97, No. 2, Feb. 1, 2009, pp. 313-331.

Guvenc et al., "A Survey on TOA Based Wireless Localization and NLOA Mitigation Techniques", IEEE Communications Surveys, IEEE, New York, NY, US, vol. 11, No. 3, Oct. 1, 2009, pp. 107-124.

Teixeira et al., "Tasking Networked CCTV Cameras and Mobile Phones to Identify and Localize Multiple People," Ubicomp '10 Proceedings of the 12th ACM International Conference on Ubiquitous Computing, Sep. 26-29, 2010, pp. 213-222.

Swedberg, "N.J. Company Seeks to Market Passive Sensor RFID Tags", RFID Journal, Jun. 14, 2011, <http://www.rfidjournal.com/articles/pdf?8527>.

Bahle et al., "I See You: How to Improve Wearable Activity Recognition by Leveraging Information from Environmental Cameras," Pervasive Computing and Communications Workshops, IEEE International Conference, Mar. 18-22, 2013.

(56) References Cited

OTHER PUBLICATIONS

Swedberg, "USDA Researchers Develop System to Track Livestock Feeding Behavior Unobtrusively", RFID Journal, Jul. 18, 2013.
U.S. Appl. No. 61/895,548, filed Oct. 25, 2013, in re: Alonso et al., entitled "Method, Apparatus, and Computer Program Product for Collecting Sporting Event Data Based on Real Time Data for Proximity and Movement of Objects".
Wang et al., "An Algorithmic and Systematic Approach from Improving Robustness of TOA-Based Localization", 2013 IEEE 10th International Conference on High Performance Computing and Communications & 2013 IEEE, Nov. 13, 2013, pp. 2066-2073.
U.S. Appl. No. 14/296,703, filed Jun. 5, 2014; in re: Alonso et al., entitled "Method and Apparatus for Associating Radio Frequency Identification Tags with Participants".
International Search Report and Written Opinion for International Application No. PCT/US2014/041062 dated Oct. 1, 2014.
International Search Report and Written Opinion for International Application No. PCT/US2014/040947 dated Oct. 9, 2014.
International Search Report and Written Opinion for International Application No. PCT/US2014/040881 dated Nov. 4, 2014.
International Search Report and Written Opinion for International Application No. PCT/US2014/040940 dated Dec. 17, 2014.
International Search Report and Written Opinion for International Application No. PCT/US2014/053647 dated Dec. 19, 2014.
Complaint before the United States District Court of Massachusetts, Civil Action No. 1:15-cv-12297, *Lynx Systems Developers, Inc. et al.* v. *Zebra Enterprise Solutions Corporation et al.*, filed Jun. 10, 2015.
International Search Report and Written Opinion for International Application No. PCT/IB2015/054213 dated Aug. 6, 2015.
International Search Report and Written Opinion for International Application No. PCT/IB2015/054103 dated Aug. 14, 2015.
International Search Report and Written Opinion for International Application No. PCT/US2015/034267 dated Sep. 25, 2015.
Invitation to Pay Additional Fees/Partial International Search Report for PCT/IB2015/054099 dated Oct. 6, 2015.
International Search Report and Written Opinion for International Application No. PCT/IB2015/054102 dated Nov. 4, 2015.
International Search Report and Written Opinion for International Application No. PCT/IB2015/054099 dated Dec. 9, 2015.
"Seattleite wins top prize in Microsoft's Super Bowl tech Contest", San Francisco AP, Komonews.com, Feb. 6, 2016. <http://komonews.com/news/local/seattleite-wins-top-prize-in-microsofts-super-bowl-tech-contest>.
International Search Report and Written Opinion for International Application No. PCT/IB2015/059264 dated Feb. 10, 2016.
Complaint before the United States District Court of Massachusetts, Civil Action No. 1:15-cv-12297, *Lynx Systems Developers, Inc. et al.* v. *Zebra Enterprise Solutions Corporation et al.*, filed Mar. 23, 2016.
Defendant's Answer to Complaint before the United States District Court of Massachusetts, Civil Action No. 1:15-cv-12297, *Lynx Systems Developers, Inc. et al.* v. *Zebra Enterprise Solutions Corporation et al.*, filed Apr. 6, 2016.
International Search Report and Written Opinion for International Application No. PCT/US2016/035614 dated Sep. 15, 2016.

\* cited by examiner

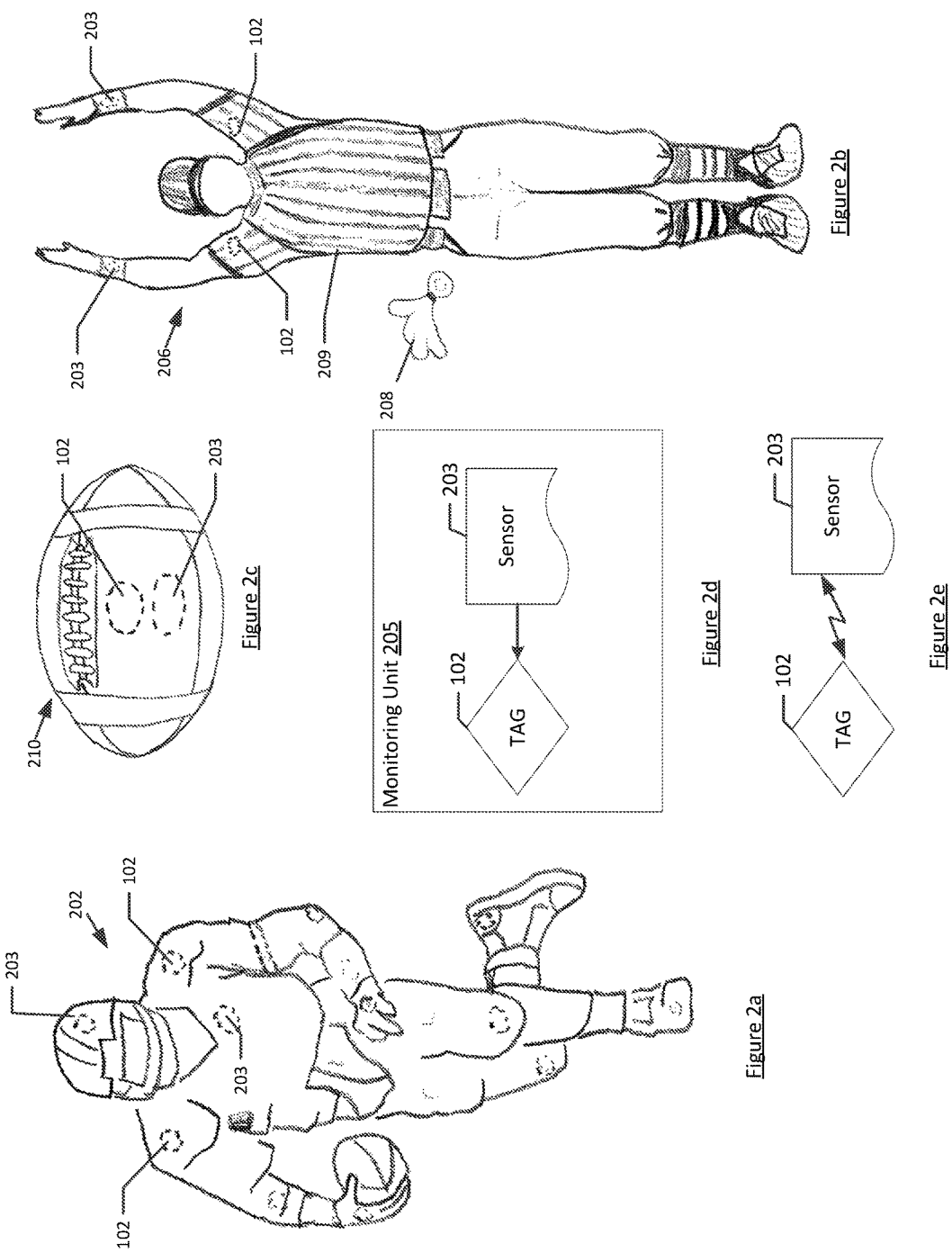

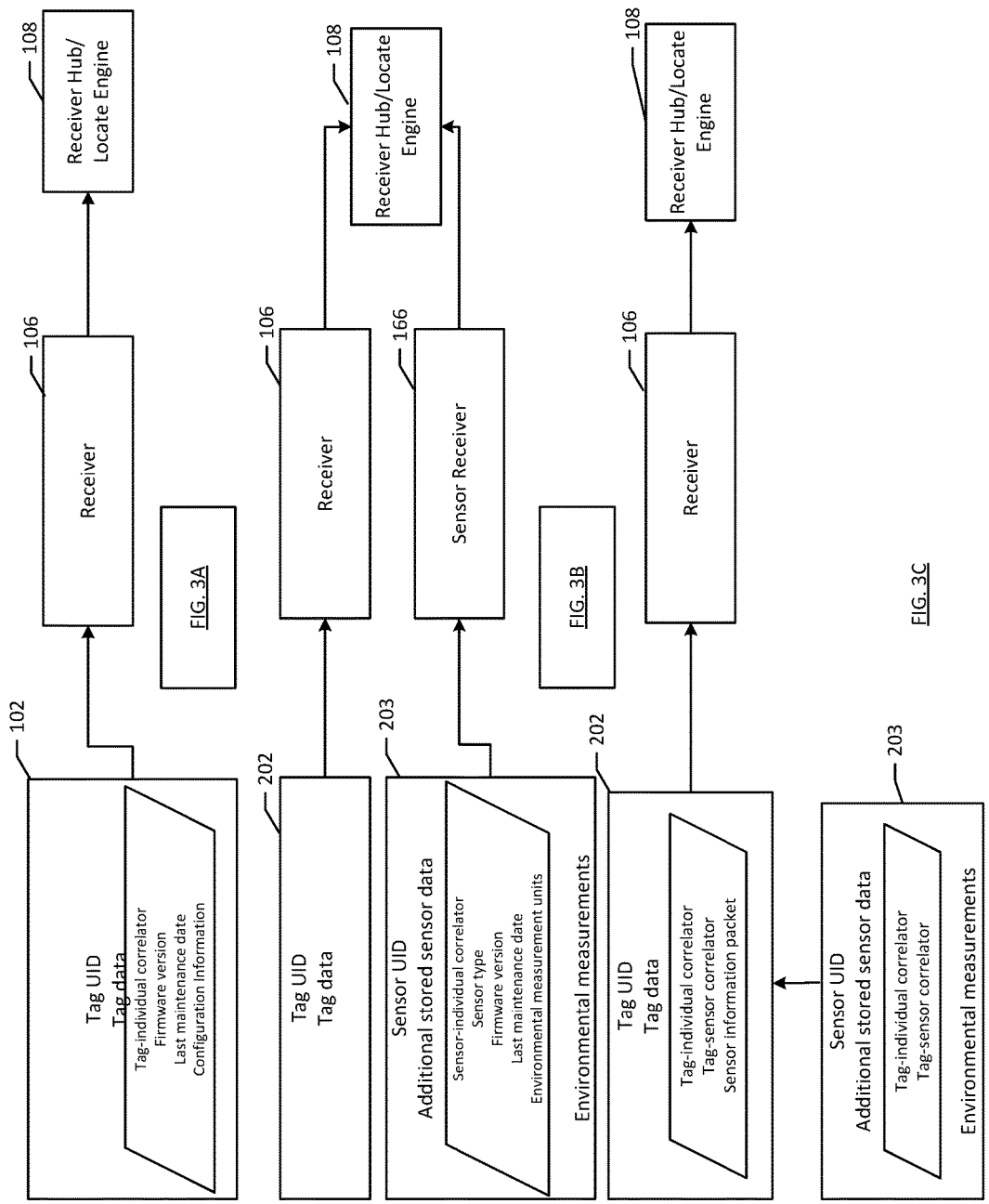

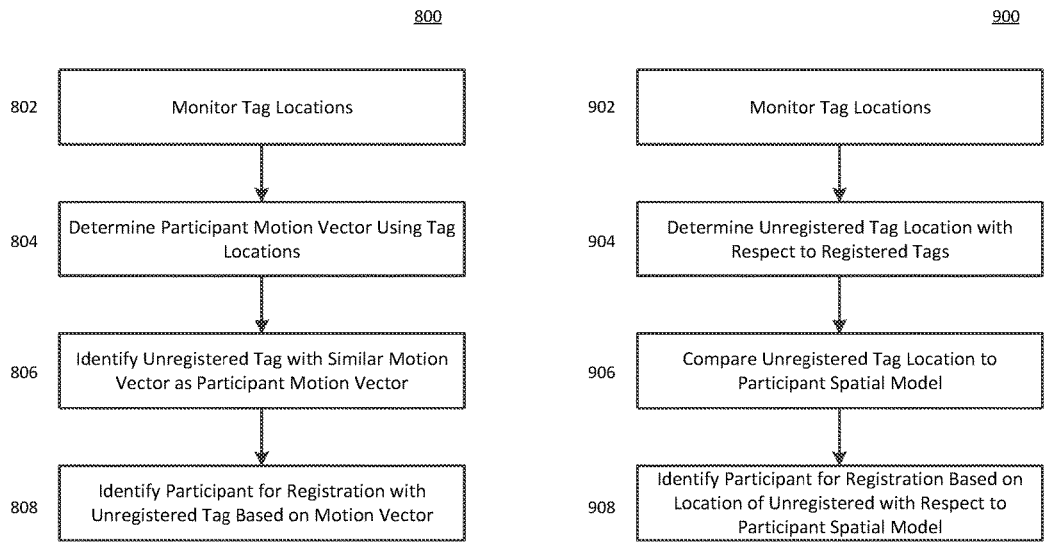
Figure 8
Figure 9
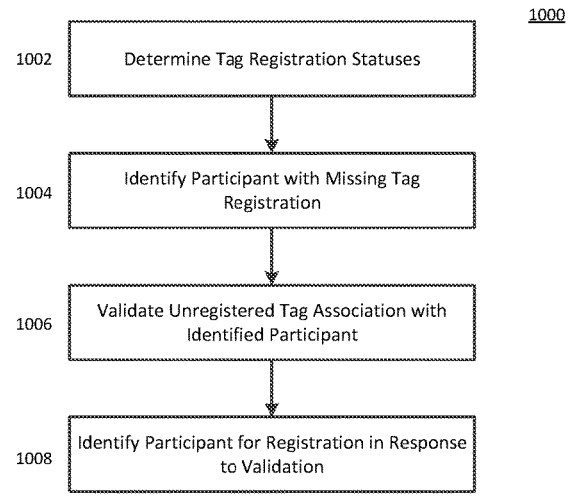
Figure 10

METHOD, APPARATUS, AND COMPUTER PROGRAM PRODUCT IMPROVING REGISTRATION WITH REAL TIME LOCATION SERVICES

CROSS REFERENCE TO RELATED APPLICATIONS

This patent arises from a continuation of U.S. patent application Ser. No. 14/298,396, filed Jun. 6, 2014, which claims priority to U.S. Provisional Application No. 61/831,990, filed Jun. 6, 2013, which are both incorporated herein by reference in their entireties.

FIELD

Embodiments discussed herein are related to radio frequency locating and, more particularly, to systems, methods, apparatus, computer readable media for improving registration of location tags within a real time location system (RTLS).

BACKGROUND

A number of deficiencies and problems associated with RTLS locating are identified herein. Through applied effort, ingenuity, and innovation, exemplary solutions to many of these identified problems are embodied by the present invention, which is described in detail below.

BRIEF SUMMARY

Systems, methods, apparatus, and computer readable media are disclosed for improving real time location systems (RTLS) with multiple location technologies. In some embodiments a method is provided for registering a participant with a radio frequency (RF) location tag. The method may include determining tag derived data from the one or more registered RF location tags, identifying at least one unregistered RF location tag, determining, using a processor, an identity of a participant for registration with the unregistered RF location tag based at least in part on the tag derived data from the one or more registered RF location tag, and registering the unregistered RF location tag with the participant. The method may also include receiving tag registration information for one or more registered RF location tags, wherein the identity of the participant is determined based at least in part on the tag registration information. The tag derived data may be a location of the one or more registered RF location tags. In some embodiments the method may also include determining a first motion vector for the participant using the tag derived data, determining a second motion vector for the unregistered RF location tag, and identifying the participant by matching the first motion vector with the second motion vector. In some embodiments, the method may include receiving a plurality of tag association models associated with a plurality of participants. Each tag association model may include a number of RF location tags associated with each respective participant. The method may also include determining the identity of the participant based at least in part on the tag association model associated with the participant. Each tag association model may also include one or more relative spatial locations between RF location tag locations associated with each respective participant, and the method may also include determining the identity of the participant based at least in part by comparing a locations of the unregistered RF location tag with a location of one or more of the registered RF location tags and with the relative spatial locations of the RF location tag locations of the tag association model corresponding to the participant.

The tag derived data may include information sufficient to determine whether a corresponding registered RF location tag is registered, and the method may further include determining the identity of the participant based at least in part on the fact that the participant has less than a minimum number of associated registered RF location tags registered to the participant. The method may also include validating the registration of the participant with the unregistered RF location tag at least in part by comparing the location of the unregistered RF location tag with the location of the registered RF location tags. The unregistered RF location tag may be an ultra-wideband (UWB) transmitter. In some embodiments, the UWB transmitter is configured to transmit a plurality of time of arrival (TOA) timing pulses. The UWB transmitter may be configured to transmit an information packet comprising 112 bits.

Further embodiments may provide an apparatus for registering a participant with a radio frequency (RF) location tag. The apparatus may include a processor coupled to a memory, the memory comprising instructions that, when executed by the apparatus, configure the apparatus. The instructions may configure the apparatus to determine tag derived data from the one or more registered RF location tags, identify at least one unregistered RF location tag, determine an identity of a participant for registration with the unregistered RF location tag based at least in part on the tag derived data from the one or more registered RF location tags, and register the unregistered RF location tag with the participant. The apparatus may be further configured to receive tag registration information for one or more registered RF location tags, and wherein the identity of the participant is determined based at least in part on the tag registration information. The tag derived data may be a location of the one or more registered RF location tags. The apparatus may be further configured to determine a first motion vector for the participant using the tag derived data, to determine a second motion vector for the unregistered RF location tag, and to identify the participant by matching the first motion vector with the second motion vector. In some embodiments, the apparatus is also configured to receive a plurality of tag association models associated with a plurality of participants. Each tag association model may include a number of RF location tags associated with each respective participant. The apparatus may also be configured to determine the identity of the participant based at least in part on the tag association model associated with the participant.

Each tag association model may include one or more relative spatial locations between RF location tag locations associated with each respective participant, and the apparatus may be configured to determine the identity of the participant based at least in part by comparing a locations of the unregistered RF location tag with a location of one or more of the registered RF location tags and with the relative spatial locations of the RF location tag locations of the tag association model corresponding to the participant. The tag derived data may include information sufficient to determine whether a corresponding registered RF location tag is registered, and the apparatus may be further configured to determine the identity of the participant based at least in part on the fact that the participant has less than a minimum number of associated registered RF location tags registered to the participant. In some embodiments, the apparatus may be further configured to validate the registration of the participant with the unregistered RF location tag at least in part by comparing the location of the unregistered RF location tag with the location of the registered RF location tags. The unregistered RF location tag may be an ultra-wideband (UWB) transmitter. The UWB transmitter may be configured to transmit a plurality of time of arrival (TOA) timing pulses. The UWB transmitter may be configured to transmit an information packet comprising 112 bits.

Yet further embodiments may provide a computer program product comprising a non-transitory computer readable storage medium. The non-transitory computer readable storage medium may include instructions that, when executed by a processor, configure an apparatus to determine tag derived data from the one or more registered RF location tags, identify at least one unregistered RF location tag, determine an identity of a participant for registration with the unregistered RF location tag based at least in part on the tag derived data from the one or more registered RF location tags, and register the unregistered RF location tag with the participant. The apparatus may be further configured by the instructions to receive tag registration information for one or more registered RF location tags, and the identity of the participant may be determined based at least in part on the tag registration information.

The tag derived data may be a location of the one or more registered RF location tags. The instructions may further configure the apparatus to determine a first motion vector for the participant using the tag derived data, determine a second motion vector for the unregistered RF location tag, and identify the participant by matching the first motion vector with the second motion vector. In yet further embodiments, the instructions may further configure the apparatus to receive a plurality of tag association models associated with a plurality of participants. Each tag association model may include a number of RF location tags associated with each respective participant. The instructions may further configure the apparatus to determine the identity of the participant based at least in part on the tag association model associated with the participant. Each tag association model further may include one or more relative spatial locations between RF location tag locations associated with each respective participant, and the instructions may further configure the apparatus to determine the identity of the participant based at least in part by comparing a locations of the unregistered RF location tag with a location of one or more of the registered RF location tags and with the relative spatial locations of the RF location tag locations of the tag association model corresponding to the participant. The tag derived data may include information sufficient to determine whether a corresponding registered RF location tag is registered, and the instructions may further configure the apparatus to determine the identity of the participant based at least in part on the fact that the participant has less than a minimum number of associated registered RF location tags registered to the participant. In some embodiments, the instructions may further configure the apparatus to validate the registration of the participant with the unregistered RF location tag at least in part by comparing the location of the unregistered RF location tag with the location of the registered RF location tags.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 illustrates an exemplary environment equipped with a radio frequency locating system and sensors for determining a participant location in accordance with some embodiments of the present invention;

FIGS. 2A-E illustrate some exemplary tags and sensor configurations that may provide information for participant location or position determination in accordance with some embodiments of the present invention;

FIGS. 3A-3E are block diagrams showing the input and output of receivers and sensor receivers in accordance with some embodiments of the present invention;

Figure 6:
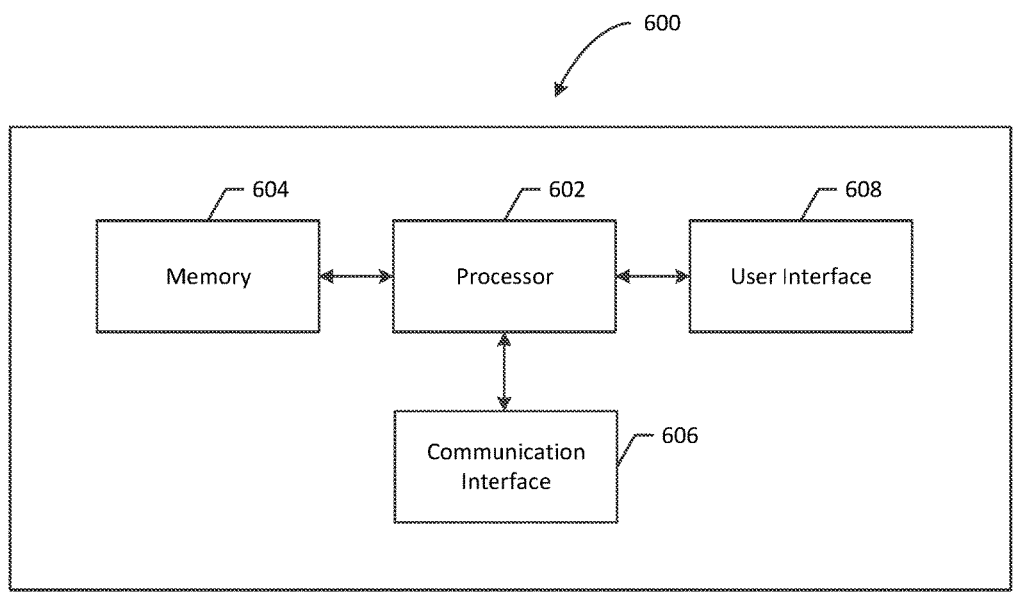
Figure 7:
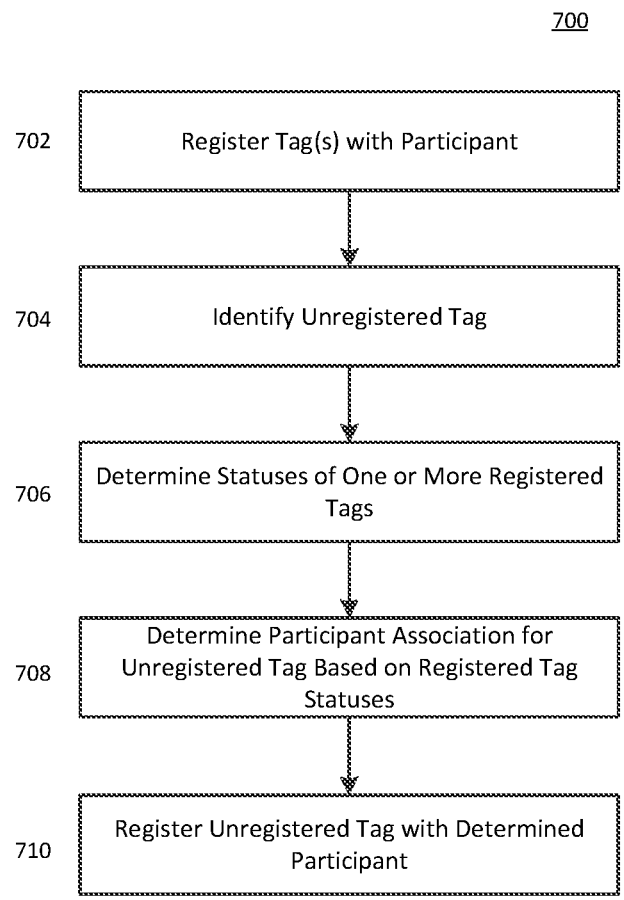
Figure 11:
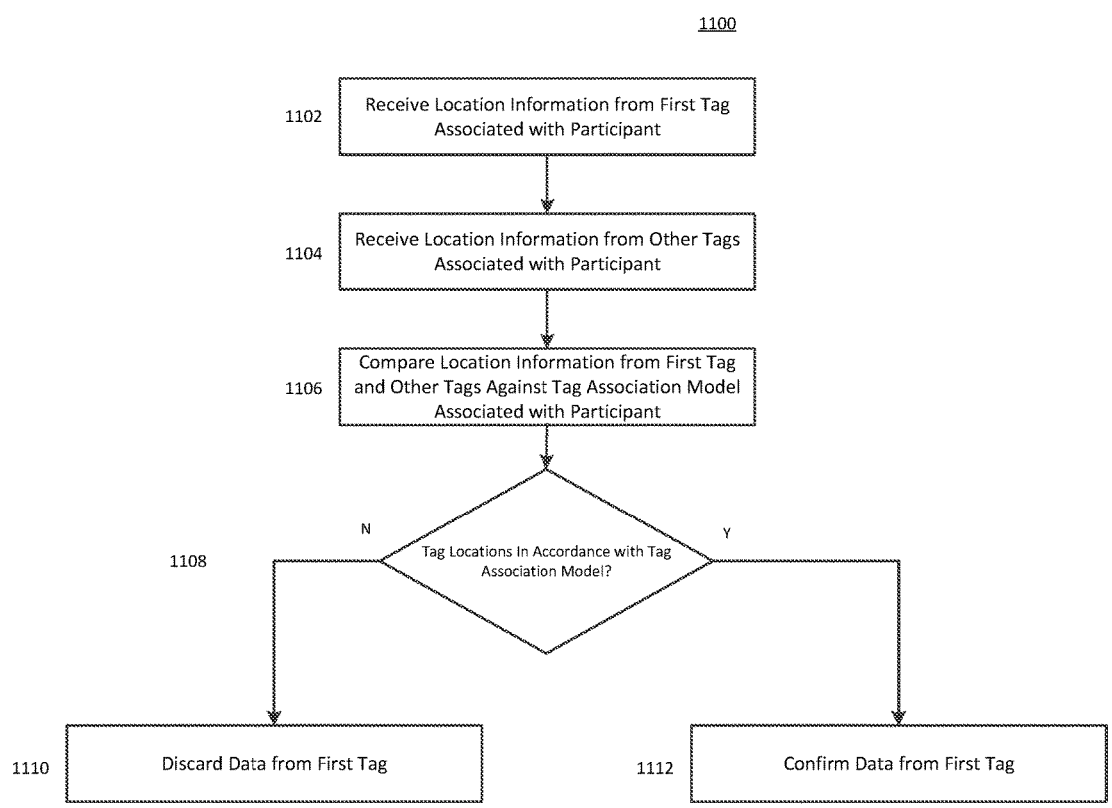

FIGS. 5A-D illustrate an exemplary tag activation process with respect to a participant in accordance with some example embodiments of the present invention;

FIG. 6 illustrates an exemplary block diagram of processing components of a location system in accordance with some example embodiments of the present invention; and FIG. 7 illustrates a flowchart of an exemplary process for registering an unregistered tag based on the status of one or more registered tags in accordance with some example embodiments of the present invention;

FIGS. 8-10 illustrate flowcharts of exemplary processes for determining a participant for registration of an unregistered tag based on the status of one or more registered tags; and FIG. 11 illustrates a flowchart of an exemplary process for using a tag association model to detect erroneous data in accordance with example embodiments of the present invention.

DETAILED DESCRIPTION

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Preliminary Definitions

A "tag", "location tag", "RF location tag" or "locate tag" refers to an ultra-wide band (UWB) transmitter that transmits a signal comprising a burst (e.g., 72 pulses at a burst rate of 1 Mb/s), and optionally, a burst having a tag data packet that may include tag data elements that may include, but are not limited to, a tag unique identification number (tag UID), other identification information, a sequential burst count, stored tag data, or other desired information for object or personnel identification, inventory control, etc. Transmitted tag signals are referred to herein as "blink data".

A "sensor" refers to any device that may collect and/or transmit data. Such devices may include, without limitation, position triangulation devices such as global positioning systems (GPS), proximity detectors, accelerometers, magnetometers, time-of-flight sensors, health monitoring sensors (e.g., blood pressure sensors, heart monitors, respiration sensors, moisture sensors, temperature sensors), light sensors, microphones, or the like.

Tags and sensors may be separate units or may be housed in a single monitoring unit. In some instances, the tag is configured to be in data communication with a sensor. Further, a tag may be configured to be in communication with a short range low frequency receiver. Tags and sensors may be associated with each other based on proximate mounting position on a participant or by a tag-sensor correlator, which is discussed in detail below. Additionally or alternatively, tags and sensors may be associated in a database, perhaps during a registration step, by a receiver hub or receiving processing and distribution system.

The terms "registered," and "registration" refers to the process by which a tag is associated with a particular participant, such as in a database. Tags that are not associated with a particular participant may be considered "unregistered". Tags that are associated with a particular participant may be considered "registered". The term "activation" refers to the process by which a tag is configured to provide blink data. For example, activation of a tag may include sending a signal to the tag that causes the tag to periodically "blink" to indicate its location to a receiver. Tags may initially be "deactivated" or "unactivated" until receipt of an activation signal. Similarly, tags may be "activated" until receiving a deactivation signal or until a power source of the tag depletes to the point where the tag can no longer provide data to a location system. In some embodiments, a tag may be deactivated until receiving an activation signal, then become activated, then return to deactivation when the activation signal stops. In some embodiments, a tag may be deactivated until receiving an activation signal, then become activated, then return to deactivation after a time period has elapsed.

The term "location data" or "locate data" refers to a location determined by the location system based on blink data transmissions received from a location tag by receivers.

The term "position data" refers to data received from sensors that may be used to determine a position calculation data or position of a sensor, which is not based on location tag blink data transmissions. Examples may include triangulation positioning data, such as global positioning, telemetry data, or the like.

The term "participant data" may include, without limitation, team name, team code, player name, player number, tag identification (e.g., tag UID) assigned to left shoulder, tag identification assigned to right shoulder, or the like. Participant data may be searched or filtered by team name, team identification, player number, player name, player role (e.g., the player's assigned field role, such as wide receiver, quarterback, offensive tackle, linebacker, defensive end, cornerback, or the like) or the like. Participant data entries may be edited by adding players/participants, updating an existing player, deleting a player, associating a tag, disassociating a tag, or the like. If a participant data is associated with a tag 102, a deletion may be allowed, but a prompt may be included indicating an existing tag association. In some examples, if the user selects "yes" the participant and tag data are deleted, if the user selects "no" the data may not be allowed to be deleted.

The terms "participant profile" and "role data" may refer to pre-defined data stored in association with the unique tag or sensor identifiers. In other embodiments, the participant profile or role data may also be "learned" by the system as a result of received tag or sensor data, formation data, play data, event data, and/or the like. For example, in some embodiments the system may determine that a tag or sensor is not correlated to a participant profile and may analyze data received from the tag and/or sensor to determine possible participant roles, etc., which may be ranked and then selected/confirmed by the system or by a user after being displayed by the system. In some embodiments, the system may determine possible participant roles (i.e., participant role data) based on determined participant location data (e.g., movement patterns, alignment position, etc.).

Overview

Systems that identify the location of entities using Radio Frequency Identification (RFID) tags may include the use of multiple tags per participant to establish an accurate location of the participant. However, in order to track the participant using those tags, the tags may first be registered with that particular participant, and then activated to begin tracking the participant. For the purposes of this application, the term "associate" or "association" when described in relation to associating a tag with a participant may encompass the process of registering the tag with respect to the particular participant. In some embodiments, the association process may also include activating the tag, though in other embodiments (e.g., when a tag is replaced during an event), tags may be activated prior to association. Existing techniques for associating tags with particular entities may be inadequate in environments with many active tags due to range limitations of devices used to program or activate the tags. Furthermore, it would be advantageous to simplify the process of selecting a particular participant with which to associate the tag to increase efficiency in reassignment, replacement, maintenance, and initial association of tags with particular participants.

For example, in a professional sports environment, it may not be feasible to ask a player to switch out his equipment during a game due to a malfunctioning RF location tag. As players congregate on the sidelines or in a bench area, it may be difficult to associate a particular tag with a particular player due to cross-talk and interference generated from RF location tags associated with all of the players in close proximity to one another and other electronic equipment, radios, cameras, and phones. Players may be reluctant to leave the game to separate themselves from the interference or to replace a malfunctioning tag. Some example embodiments provide for the use of status information from one or more registered tags to inform the registration database of unregistered tags. Such embodiments may advantageously provide for automatic and/or programmatic registration of tags, thus increasing the efficiency of tag replacement operations. As such, example embodiments advantageously provide for systems and methods that reduce the complexity of the process of associating a particular RF location tag or set of tags with a particular participant.

Example Real Time Locating System

Figure 1:
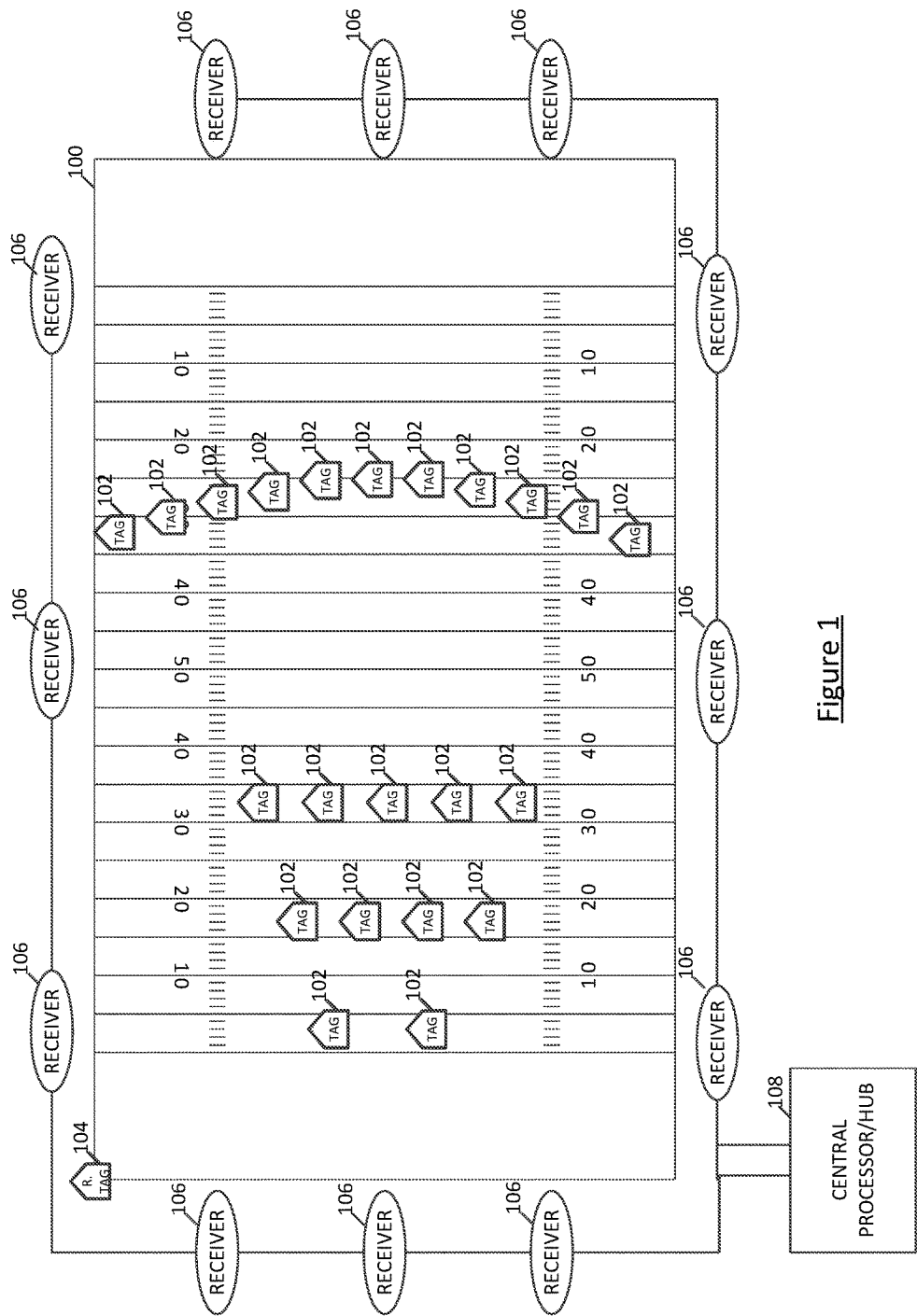

FIG. 1 illustrates an exemplary locating system 100 useful for calculating a location by an accumulation of position data or time of arrivals (TOAs) at a central processor/Hub 108, whereby the TOAs represent a relative time of flight (TOF) from RTLS tags 102 as recorded at each receiver 106 (e.g., UWB reader, etc.). A timing reference clock is used, in some examples, such that at least a subset of the receivers 106 may be synchronized in frequency, whereby the relative TOA data associated with each of the RTLS tags 102 may be registered by a counter associated with at least a subset of the receivers 106. In some examples, a reference tag 104, preferably a UWB transmitter, positioned at known coordinates, is used to determine a phase offset between the counters associated with at least a subset of the of the receivers 106. The RTLS tags 102 and the reference tags 104 reside in an active RTLS field. The systems described herein may be referred to as either "multilateration" or "geolocation" systems, terms that refer to the process of locating a signal source by solving an error minimization function of a location estimate determined by the difference in time of arrival (DTOA) between TOA signals received at multiple receivers 106.

In some examples, the system comprising at least the tags 102 and the receivers 106 is configured to provide two dimensional and/or three dimensional precision localization (e.g., subfoot resolutions), even in the presence of multipath interference, due in part to the use of short nanosecond duration pulses whose TOF can be accurately determined using detection circuitry, such as in the receivers 106, which can trigger on the leading edge of a received waveform. In some examples, this short pulse characteristic allows necessary data to be conveyed by the system at a higher peak power, but lower average power levels, than a wireless system configured for high data rate communications, yet still operate within local regulatory requirements.

In some examples, to provide a preferred performance level while complying with the overlap of regulatory restrictions (e.g. FCC and ETSI regulations), the tags 102 may operate with an instantaneous −3 dB bandwidth of approximately 400 MHz and an average transmission below 187 pulses in a 1 msec interval, provided that the packet rate is sufficiently low. In such examples, the predicted maximum range of the system, operating with a center frequency of 6.55 GHz, is roughly 200 meters in instances in which a 12 dBi directional antenna is used at the receiver, but the projected range will depend, in other examples, upon receiver antenna gain. Alternatively or additionally, the range of the system allows for one or more tags 102 to be detected with one or more receivers positioned throughout a football stadium used in a professional football context. Such a configuration advantageously satisfies constraints applied by regulatory bodies related to peak and average power densities (e.g., effective isotropic radiated power density ("EIRP")), while still optimizing system performance related to range and interference. In further examples, tag transmissions with a −3 dB bandwidth of approximately 400 MHz yields, in some examples, an instantaneous pulse width of roughly 2 nanoseconds that enables a location resolution to better than 30 centimeters.

Referring again to FIG. 1, the object to be located has an attached tag 102, preferably a tag having a UWB transmitter, that transmits a burst (e.g., multiple pulses at a 1 Mb/s burst rate, such as 112 bits of On-Off keying (OOK) at a rate of 1 Mb/s), and optionally, a burst comprising an information packet utilizing OOK that may include, but is not limited to, ID information, a sequential burst count or other desired information for object or personnel identification, inventory control, etc. In some examples, the sequential burst count (e.g., a packet sequence number) from each tag 102 may be advantageously provided in order to permit, at a Central Processor/Hub 108, correlation of TOA measurement data from various receivers 106.

In some examples, the tag 102 may employ UWB waveforms (e.g., low data rate waveforms) to achieve extremely fine resolution because of their extremely short pulse (i.e., sub-nanosecond to nanosecond, such as a 2 nsec (1nsec up and 1nsec down)) durations. As such, the information packet may be of a short length (e.g. 112 bits of OOK at a rate of 1 Mb/sec, in some example embodiments), that advantageously enables a higher packet rate. If each information packet is unique, a higher packet rate results in a higher data rate; if each information packet is transmitted repeatedly, the higher packet rate results in a higher packet repetition rate. In some examples, higher packet repetition rate (e.g., 12 Hz) and/or higher data rates (e.g., 1 Mb/sec, 2 Mb/sec or the like) for each tag may result in larger datasets for filtering to achieve a more accurate location estimate. Alternatively or additionally, in some examples, the shorter length of the information packets, in conjunction with other packet rate, data rates and other system requirements, may also result in a longer battery life (e.g., 7 years battery life at a transmission rate of 1 Hz with a 300 mAh cell, in some present embodiments).

Tag signals may be received at a receiver directly from RTLS tags, or may be received after being reflected en route. Reflected signals travel a longer path from the RTLS tag to the receiver than would a direct signal, and are thus received later than the corresponding direct signal. This delay is known as an echo delay or multipath delay. If reflected signals are sufficiently strong enough to be detected by the receiver, they can corrupt a data transmission through inter-symbol interference. In some examples, the tag 102 may employ UWB waveforms to achieve extremely fine resolution because of their extremely short pulse (e.g., 2 nsec) durations. Furthermore, signals may comprise short information packets (e.g., 112 bits of OOK) at a somewhat high burst data rate (1 Mb/sec, in some example embodiments), that advantageously enable packet durations to be brief (e.g. 112 microsec) while allowing inter-pulse times (e.g., 998 nsec) sufficiently longer than expected echo delays, avoiding data corruption.

Reflected signals can be expected to become weaker as delay increases due to more reflections and the longer distances traveled. Thus, beyond some value of inter-pulse time (e.g., 998 nsec), corresponding to some path length difference (e.g., 299.4 m.), there will be no advantage to further increases in inter-pulse time (and, hence lowering of burst data rate) for any given level of transmit power. In this manner, minimization of packet duration allows the battery life of a tag to be maximized, since its digital circuitry need only be active for a brief time. It will be understood that different environments can have different expected echo delays, so that different burst data rates and, hence, packet durations, may be appropriate in different situations depending on the environment.

Minimization of the packet duration also allows a tag to transmit more packets in a given time period, although in practice, regulatory average EIRP limits may often provide an overriding constraint. However, brief packet duration also reduces the likelihood of packets from multiple tags overlapping in time, causing a data collision. Thus, minimal packet duration allows multiple tags to transmit a higher aggregate number of packets per second, allowing for the largest number of tags to be tracked, or a given number of tags to be tracked at the highest rate.

In one non-limiting example, a data packet length of 112 bits (e.g., OOK encoded), transmitted at a data rate of 1 Mb/sec (1 MHz), may be implemented with a transmit tag repetition rate of 1 transmission per second (1 TX/sec). Such an implementation may accommodate a battery life of up to seven years, wherein the battery itself may be, for example, a compact, 3-volt coin cell of the series no. BR2335 (Rayovac), with a battery charge rating of 300 mAhr. An alternate implementation may be a generic compact, 3-volt coin cell, series no. CR2032, with a battery charge rating of 220 mAhr, whereby the latter generic coin cell, as can be appreciated, may provide for a shorter battery life.

Alternatively or additionally, some applications may require higher transmit tag repetition rates to track a dynamic environment. In some examples, the transmit tag repetition rate may be 12 transmissions per second (12 TX/sec). In such applications, it can be further appreciated that the battery life may be shorter.

The high burst data transmission rate (e.g., 1 MHz), coupled with the short data packet length (e.g., 112 bits) and the relatively low repetition rates (e.g., 1 TX/sec), provide for two distinct advantages in some examples: (1) a greater number of tags may transmit independently from the field of tags with a lower collision probability, and/or (2) each independent tag transmit power may be increased, with proper consideration given to a battery life constraint, such that a total energy for a single data packet is less than a regulated average power for a given time interval (e.g., a 1 msec time interval for an FCC regulated transmission).

Alternatively or additionally, additional sensor or telemetry data may be transmitted from the tag to provide the receivers 106 with information about the environment and/or operating conditions of the tag. For example, the tag may transmit a temperature to the receivers 106. Such information may be valuable, for example, in a system involving perishable goods or other refrigerant requirements. In this example embodiment, the temperature may be transmitted by the tag at a lower repetition rate than that of the rest of the data packet. For example, the temperature may be transmitted from the tag to the receivers at a rate of one time per minute (e.g., 1 TX/min.), or in some examples, once every 720 times the data packet is transmitted, whereby the data packet in this example is transmitted at an example rate of 12 TX/sec.

Alternatively or additionally, the tag 102 may be programmed to intermittently transmit data to the receivers 106 in response to a signal from a magnetic command transmitter (not shown). The magnetic command transmitter may be a portable device, functioning to transmit a 125 kHz signal, in some example embodiments, with a range of approximately 15 feet or less, to one or more of the tags 102. In some examples, the tags 102 may be equipped with at least a receiver tuned to the magnetic command transmitter transmit frequency (e.g., 125 kHz) and functional antenna to facilitate reception and decoding of the signal transmitted by the magnetic command transmitter.

In some examples, one or more other tags, such as a reference tag 104, may be positioned within and/or about a monitored region. In some examples, the reference tag 104 may be configured to transmit a signal that is used to measure the relative phase (e.g., the count of free-running counters) of non-resettable counters within the receivers 106.

One or more (e.g., preferably four or more) receivers 106 are also positioned at predetermined coordinates within and/or around the monitored region. In some examples, the receivers 106 may be connected in a "daisy chain" fashion to advantageously allow for a large number of receivers 106 to be interconnected over a significant monitored region in order to reduce and simplify cabling, provide power, and/or the like. Each of the receivers 106 includes a receiver for receiving transmissions, such as UWB transmissions, and preferably, a packet decoding circuit that extracts a time of arrival (TOA) timing pulse train, transmitter ID, packet number, and/or other information that may have been encoded in the tag transmission signal (e.g., material description, personnel information, etc.) and is configured to sense signals transmitted by the tags 102 and one or more reference tags 104.

Each receiver 106 includes a time measuring circuit that measures times of arrival (TOA) of tag bursts, with respect to its internal counter. The time measuring circuit is phase-locked (e.g., phase differences do not change and therefore respective frequencies are identical) with a common digital reference clock signal distributed via cable connection from a Central Processor/Hub 108 having a central timing reference clock generator. The reference clock signal establishes a common timing reference for the receivers 106. Thus, multiple time measuring circuits of the respective receivers 106 are synchronized in frequency, but not necessarily in phase. While there typically may be a phase offset between any given pair of receivers in the receivers 106, the phase offset is readily determined through use of a reference tag 104. Alternatively or additionally, each receiver may be synchronized wirelessly via virtual synchronization without a dedicated physical timing channel.

In some example embodiments, the receivers 106 are configured to determine various attributes of the received signal. Since measurements are determined at each receiver 106, in a digital format, rather than analog in some examples, signals are transmittable to the Central Processor/Hub 108. Advantageously, because packet data and measurement results can be transferred at high speeds to a receiver memory, the receivers 106 can receive and process tag (and corresponding object) locating signals on a nearly continuous basis. As such, in some examples, the receiver memory allows for a high burst rate of tag events (i.e., information packets) to be captured.

Data cables or wireless transmissions may convey measurement data from the receivers 106 to the Central Processor/Hub 108 (e.g., the data cables may enable a transfer speed of 2 Mbps). In some examples, measurement data is transferred to the Central Processor/Hub at regular polling intervals.

As such, the Central Processor/Hub 108 determines or otherwise computes tag location (i.e., object position) by processing TOA measurements relative to multiple data packets detected by the receivers 106. In some example embodiments, the Central Processor/Hub 108 may be configured to resolve the coordinates of a tag using nonlinear optimization techniques.

In some examples, TOA measurements from multiple receivers 106 are processed by the Central Processor/Hub 108 to determine a position of the transmit tag 102 by a differential time-of-arrival (DTOA) analysis of the multiple TOAs. The DTOA analysis includes a determination of tag transmit time $t_0$, whereby a time-of-flight (TOF), measured as the time elapsed from the estimated tag transmit time $t_0$ to the respective TOA, represents graphically the radii of spheres centered at respective receivers 106. The distance between the surfaces of the respective spheres to the estimated position coordinates $(x_0, y_0, z_0)$ of the transmit tag 102 represents the measurement error for each respective TOA, and the minimization of the sum of the squares of the TOA measurement errors from each receiver participating in the DTOA position estimate provides for both the position coordinates (xo, yo, zo) of the transmit tag and of that tag's transmit time $t_0$.

In some examples, the system described herein may be referred to as an "over-specified" or "over-determined" system. As such, the Central Processor/Hub 108 may calculate one or more valid (i.e., most correct) positions based on a set of measurements and/or one or more incorrect (i.e., less correct) positions. For example, a position may be calculated that is impossible due the laws of physics or may be an outlier when compared to other calculated positions. As such one or more algorithms or heuristics may be applied to minimize such error.

The starting point for the minimization may be obtained by first doing an area search on a coarse grid of x, y and z over an area defined by the user and followed by a localized steepest descent search. The starting position for this algorithm is fixed, in some examples, at the mean position of all active receivers. No initial area search is needed, and optimization proceeds through the use of a Davidon-Fletcher-Powell (DFP) quasi-Newton algorithm in some examples. In other examples, a steepest descent algorithm may be used.

One such algorithm for error minimization, which may be referred to as a time error minimization algorithm, may be described in Equation 1:

$$\varepsilon = \sum_{j=1}^{N} \left[ [(x - x_j)^2 + (y - y_j)^2 + (z - z_j)^2]^{\frac{1}{2}} - c(t_j - t_0) \right]^2 \quad (1)$$

Where N is the number of receivers, c is the speed of light, $(x_j, y_j, z_j)$ are the coordinates of the $j^{th}$ receiver, $t_j$ is the arrival time at the $j^{th}$ receiver, and $t_0$ is the tag transmit time. The variable $t_0$ represents the time of transmission. Since $t_0$ is not initially known, the arrival times, $t_j$, as well as $t_0$, are related to a common time base, which in some examples, is derived from the arrival times. As a result, differences between the various arrival times have significance for determining position as well as $t_0$.

The optimization algorithm to minimize the error $\varepsilon$ in Equation 1 may be the Davidon-Fletcher-Powell (DFP) quasi-Newton algorithm, for example. In some examples, the optimization algorithm to minimize the error 249 in Equation 1 may be a steepest descent algorithm. In each case, the algorithms may be seeded with an initial position estimate (x, y, z) that represents the two-dimensional (2D) or three-dimensional (3D) mean of the positions of the receivers 106 that participate in the tag position determination.

In some examples, the RTLS system comprises a receiver grid, whereby each of the receivers 106 in the receiver grid keeps a receiver clock that is synchronized, with an initially unknown phase offset, to the other receiver clocks. The phase offset between any receivers may be determined by use of a reference tag that is positioned at a known coordinate position $(x_T, y_T, z_T)$. The phase offset serves to resolve the constant offset between counters within the various receivers 106, as described below.

In further example embodiments, a number N of receivers 106 $\{R_j: j=1, \ldots, N\}$ are positioned at known coordinates $(x_{R_j}, y_{R_j}, z_{R_j})$ which are respectively located at distances $d_{R_j}$ from a reference tag 104, such as given in Equation 2:

$$d_{R_j} = \sqrt{(x_{R_j} - x_T)^2 + (y_{R_j} - y_T)^2 + (z_{R_j} - z_T)^2} \quad (2)$$

Each receiver $R_j$ utilizes, for example, a synchronous clock signal derived from a common frequency time base, such as a clock generator. Because the receivers are not synchronously reset, an unknown, but constant offset $O_j$ exists for each receiver's internal free running counter. The value of the constant offset $O_j$ is measured in terms of the number of fine resolution count increments (e.g., a number of nanoseconds for a one nanosecond resolution system).

The reference tag is used, in some examples, to calibrate the radio frequency locating system as follows: The reference tag emits a signal burst at an unknown time $\tau_R$. Upon receiving the signal burst from the reference tag, a count $N_{R_j}$ as measured at receiver $R_j$ is given in Equation 3 by:

$$N_{R_j} = \beta \tau_R + O_j + \beta d_{R_j}/c \quad (3)$$

Where c is the speed of light and $\beta$ is the number of fine resolution count increments per unit time (e.g., one per nanosecond). Similarly, each object tag $T_i$ of each object to be located transmits a signal at an unknown time $\tau_i$ to produce a count $N_{i_j}$, as given in Equation 4:

$$N_{i_j} = \beta \tau_i + O_j + \beta d_{ij}/c \quad (4)$$

at receiver $R_j$ where $d_{ij}$ is the distance between the object tag $T_i$ and the receiver 106 $R_j$. Note that $\tau_i$ is unknown, but has the same constant value for all receivers. Based on the equalities expressed above for receivers $R_j$ and $R_k$ and given the reference tag 104 information, phase offsets expressed as differential count values are determined as given in Equations 5a-b:

$$N_{R_j} - N_{R_k} = (O_j - O_k) + \beta \left( \frac{d_{R_j}}{c} - \frac{d_{R_k}}{c} \right) \quad (5a)$$

Or, $$(O_j - O_k) = (N_{R_j} - N_{R_k}) - \beta \left( \frac{d_{R_j}}{c} - \frac{d_{R_k}}{c} \right) = \Delta_{jk} \quad (5b)$$

Where $\Delta_{jk}$ is constant as long as $d_{R_j} - d_{R_k}$ remains constant, (which means the receivers and reference tag are fixed and there is no multipath situation) and $\beta$ is the same for each receiver. Note that $\Delta_{jk}$ is a known quantity, since $N_{R_j}$, $N_{R_k}$, $\beta$, $d_{R_j}/c$, and $d_{R_k}/c$ are known. That is, the phase offsets between receivers $R_j$ and $R_k$ may be readily determined based on the reference tag 104 transmissions. Thus, again from the above equations, for a tag 102 (T1) transmission arriving at receivers $R_j$ and $R_k$, one may deduce the following Equations 6a-b:

$$N_{i_j} - N_{i_k} = (O_j - O_k) + \beta \left( \frac{d_{i_j}}{c} - \frac{d_{i_k}}{c} \right) = \Delta_{jk} + \beta \left( \frac{d_{i_j}}{c} - \frac{d_{i_k}}{c} \right) \quad (6a)$$

Or, $$d_{i_j} - d_{i_k} = (c/\beta)[N_{i_j} - N_{i_k} - \Delta_{jk}] \quad (6b)$$

Each arrival time, $t_j$, can be referenced to a particular receiver (receiver "1") as given in Equation 7:

$$t_j = \frac{1}{\beta}(N_j - \Delta_{j1}) \quad (7)$$

The minimization, described in Equation 1, may then be performed over variables (x, y, z, $t_0$) to reach a solution (x', y', z', $t_0$').

Example Tag/Sensor Location Determination and Participant Correlation

FIGS. 2a-e illustrate some exemplary tag and sensor configurations that may provide information to a location system or over-determined location system in accordance with some embodiments of the present invention. A participant is any person, location or object to which a tag and/or sensor has been attached. FIG. 2a illustrates a participant 202, which is a football player wearing equipment having attached tags 102 in accordance with some embodiments. In particular, the depicted participant 202 is wearing shoulder pads having tags 102 affixed to opposite sides thereof. This positioning advantageously provides an elevated broadcast location for each tag 102 thereby increasing its communication effectiveness. Additional sensors 203 may be attached to equipment worn by participant 202, such as accelerometers, magnetometers, compasses, gyroscopes, time-of-flight sensors, health monitoring sensors (e.g., blood pressure sensors, heart monitors, respiration sensors, moisture sensors, temperature sensors), light sensors, or the like. The additional sensors 204 may be affixed to shoulder pads, the helmet, the shoes, rib pads, elbow pads, the jersey, the pants, a bodysuit undergarment, gloves, arm bands, wristbands, and the like. In some cases, additional sensors may be fastened to or implanted under the player's skin, swallowed, or otherwise be carried internally in the player's body. Sensors 204 may be configured to communicate with receivers (e.g., receivers 106 of FIG. 1) directly or indirectly through tags 102 or other transmitters. For example, in one embodiment, a sensor 203 may be connected, wired (e.g., perhaps through wires sewn into a jersey or bodysuit undergarment) or wirelessly, to tags 102 to provide sensor data to tags 102, which is then transmitted to the receivers 106. In another embodiment, a plurality of sensors (not shown) may be connected to a dedicated antenna or transmitter, perhaps located in the helmet, which may transmit sensor data to one or more receivers.

FIG. 2b illustrates a participant 206 depicted as a game official wearing equipment having attached tags 102 and sensors 203 in accordance with some embodiments. In the depicted embodiment, tags 102 are attached to the participant's jersey proximate opposite shoulders. Sensors 203 are provided in wristbands worn on the official's wrists as shown. Sensors 203 may be configured to communicate with receivers (e.g., receivers 106 of FIG. 1) directly or indirectly through tags 102 or other transmitters as discussed above in connection with FIG. 2a.

As discussed in greater detail below, the positioning of sensors 203 (here, accelerometers) proximate the wrists of the participant may allow the central processor/hub 108 to determine particular motions, movements, or activities of the official 206 for use in determining events (e.g., winding of the game clock, first down, touchdown, or the like). The participant 206 may also carry other equipment, such as penalty flag 208, which may also have a tag 102 (and optionally one or more sensors) attached to provide additional data to the central processor/hub 108. For example, central processor/hub 108may use tag location data from the penalty flag 208 to determine when the official is merely carrying the penalty flag 208 versus when the official is using the penalty flag 208 to indicate an event, such as a penalty (e.g., by throwing the penalty flag 208).

FIG. 2c illustrates an example of a participant 210 depicted as a game ball having tags 102 attached or embedded in accordance with some embodiments. Additionally, sensors 203 may be attached to or embedded in the ball 210, such as accelerometers, time-of-flight sensors, or the like. In some embodiments, the sensor 204 may be connected, wired or wirelessly, to tag 102 to provide sensor data to tag 102 which is then transmitted to the receivers 106. In some embodiments, the sensor 203 may transmit sensor data to receivers separately from the tag 102, such as described above in connection with FIG. 2a.

FIG. 2d illustrates a monitoring unit 205 including a tag 102 and a sensor 203. The tag and sensor may be embodied in a single housing or monitoring unit 205. The tag and sensor may operate independently or may be in wired or wireless communication. The senor 203 may be configured to transmit signals to the tag 102 to commence, terminate, or change the rate of blink data transmissions. The sensor 203 may send signals configured to control the tag blink data transmission by using a low frequency transceiver with a range based on the size of the monitoring unit 205.

FIG. 2e illustrates a tag 103 and sensor 203 configuration in which the tag and sensor are separate units. The tag 102 may be associated but operate independently of the sensor 203, or may be in wired or wireless communication. In an instance in which the tag 102 is in wireless communication with the sensor 203, the sensor may send control signals to control the tag blink data transmissions as discussed above in FIG. 3d. The effective range of the sensor low frequency transmission may be 12 inches, 18 inches, 24 inches, 36 inches or any other distance value. The effective range of the low frequency transmission is based on the proximate mounting locations of the tag 102 and sensor 203. In an instance in which the tag 102 and the sensor 203 are mounted in close proximity the low frequency transmission may be of a lower range and power. For example, in an instance in which the tag 102 and sensor 203 are mounted 2 inches away from each other on the back of a helmet. Similarly, the range and power of the low frequency transmission may be increased if the tag 102 and sensor are located further away from each other. For example, in an instance in which the sensor is mounted to the participant's belt at waist level, and the tag is mounted in a shoulder pad.

As will be apparent to one of ordinary skill in the art in view of this disclosure, once the tags 102 and sensors 203 of FIGS. 2a-e are located on participants, they may be correlated to such participants and/or to each other. For example, in some embodiments, unique tag or sensor identifiers ("unique IDs") may be correlated to a participant profile (e.g., John Smith—running back, Fred Johnson—line judge official, or ID 027—one of several game balls, etc.) and stored to a remote database accessible to the performance analytics system as discussed in greater detail below. Each participant profile may further include or be correlated with a variety of data including, but not limited to, biometric data (e.g., height, weight, health data, etc.), role data, team ID, performance statistics, and other data that may be apparent to one of skill in the art in view of the foregoing description.

In some embodiments, such participant profile or role data may be pre-defined and stored in association with the unique tag or sensor identifiers. In other embodiments, the participant profile or role data may also be "learned" by the system as a result of received tag or sensor data, formation data, play data, event data, and/or the like. For example, in some embodiments the system may determine that a tag or sensor is not correlated to a participant profile and may analyze data received from the tag and/or sensor to determine possible participant roles, etc., which may be ranked and then selected/confirmed by the system or by a user after being displayed by the system. In some embodiments, the system may determine possible participant roles (i.e., participant role data) based on determined participant location or position data (e.g., movement patterns, alignment position, etc.).

In some embodiments, as described in greater detail below, the participant profile or role data may also be updated by the system (i.e., to produce a data set for the participant that is far more robust than that established at initial registration) as a result of received tag or sensor data, formation data, play data, event data, and/or the like. In some embodiments, the participant profile and/or role data may be used in a performance analytics system to weight the actions of the participants during analysis to assist in qualifying what is occurring, such as in determining formations, plays, events, etc.

Tag ID and Sensor Data Transmission Architecture

FIGS. 3A, 3B, 3C, 3D, and 3E show block diagrams of various different architectures that may be utilized in transmitting signals from one or more tags and sensors to one or more receivers of a receiver processing and analytics system in accordance with embodiments of the invention. In some embodiments, the depicted architectures may be used in connection with the central processor/hub 108 of FIG. 1. More than one of these architectures may be used together in a single system.

FIG. 3A shows a RF location tag 102, such as that shown in FIG. 1, which may be configured to transmit a tag signal to one or more receivers 106. The one or more receivers 106 may transmit a receiver signal to the receiver hub/locate engine 108.

The depicted RF location tag 102 may generate or store a tag unique identifier ("tag UID") and/or tag data as shown. The tag data may include useful information such as the installed firmware version, last tag maintenance date, configuration information, and/or a tag-individual correlator. The tag-individual correlator may comprise data that indicates that a monitored individual (e.g., participant) is associated with the RF location tag 102 (e.g., name, uniform number and team, biometric data, tag assignment on individual, i.e., right wrist). As will be apparent to one of skill in the art in view of this disclosure, the tag-individual correlator may be stored to the RF location tag 102 when the tag is registered or otherwise associated with an individual. While shown as a separate field for illustration purposes, one of ordinary skill in the art may readily appreciate that the tag-individual correlator may be part of any tag data or even omitted from the tag.

The tag signal transmitted from RF location tag 102 to receiver 106 may include "blink data" as it is transmitted at selected intervals. This "blink rate" may be set by the tag designer or the system designer to meet application requirements. In some embodiments it is consistent for one or all tags; in some embodiments it may be data dependent. Blink data includes characteristics of the tag signal that allow the tag signal to be recognized by the receiver 106 so the location of the RF location tag 102 may be determined by the locating system. Blink data may also comprise one or more tag data packets. Such tag data packets may include any data from the tag 102 that is intended for transmission such as, for example in the depicted embodiment, a tag UID, tag data, and a tag-individual correlator. In the case of TDOA systems, the blink data may be or include a specific pattern, code, or trigger that the receiver 106 (or downstream receiver processing and analytics system) detects to identify that the transmission is from a RF location tag 102 (e.g., a UWB tag).

The depicted receiver 106 receives the tag signal, which includes blink data and tag data packets as discussed above. In one embodiment, the receiver 106 may pass the received tag signal directly to the receive hub/locate engine 108 as part of its receiver signal. In another embodiment, the receiver 106 could perform some basic processing on the received tag signal. For instance, the receiver could extract blink data from the tag signal and transmit the blink data to the receive hub/locate engine 108. The receiver could transmit a time measurement to the receive hub/locate engine 108 such as a TOA measurement and/or a TDOA measurement. The time measurement could be based on a clock time generated or calculated in the receiver, it could be based on a receiver offset value as explained above, it could be based on a system time, and/or it could be based on the time difference of arrival between the tag signal of the RF location tag 102 and the tag signal of a RF reference tag (e.g., tag 104 of FIG. 1). The receiver 106 could additionally or alternatively determine a signal measurement from the tag signal (such as a received signal strength indication (RSSI), a direction of signal, signal polarity, or signal phase) and transmit the signal measurement to the receive hub/locate engine 108.

FIG. 3B shows a RF location tag 202 and sensor 203, such as those worn on an individual's person as shown in FIG. 2, which may be configured to transmit tag signals and sensor signals, respectively, to one or more receivers 106, 166. The one or more receivers 106, 166 may then transmit receiver signals to the receiver hub/locate engine 108. One or more receivers 106, 166 may share physical components, such as a housing or antenna.

The depicted RF location tag 202 may comprise a tag UID and tag data (such as a tag-individual correlator) and transmit a tag signal comprising blink data as discussed in connection with FIG. 3A above. The depicted sensor 203 may generate and/or store a sensor UID, additional stored sensor data (e.g. a sensor-individual correlator, sensor type, sensor firmware version, last maintenance date, the units in which environmental measurements are transmitted, etc.), and environmental measurements. The "additional stored sensor data" of the sensor 203 may include any data that is intended for transmission, including but not limited to a RF location tag 202, a reference tag (e.g., 104 of FIG. 1), a sensor receiver, a receiver 106, and/or the receiver/hub locate engine 108.

The sensor-individual correlator may comprise data that indicates that a monitored individual is associated with the sensor 203 (e.g., name, uniform number and team, biometric data, sensor position on individual, i.e., right wrist). As will be apparent to one of skill in the art in view of this disclosure, the sensor-individual correlator may be stored to the sensor 203 when the sensor is registered or otherwise associated with an individual. While shown as a separate field for illustration purposes, one of ordinary skill in the art may readily appreciate that the sensor-individual correlator may be part of any additional stored sensor data or omitted from the sensor altogether.

Sensors such as sensor 203 that are structured according to embodiments of the invention may sense or determine one or more environmental conditions (e.g. temperature, pressure, pulse, heartbeat, rotation, velocity, acceleration, radiation, position, chemical concentration, voltage) and store or transmit "environmental measurements" that are indicative of such conditions. To clarify, the term "environmental measurements" includes measurements concerning the environment proximate the sensor including, without limitation, ambient information (e.g., temperature, position, humidity, etc.) and information concerning an individual's health, fitness, operation, and/or performance. Environmental measurements may be stored or transmitted in either analog or digital form and may be transmitted as individual measurements, as a set of individual measurements, and/or as summary statistics. For example, temperature in degrees Celsius may be transmitted as {31}, or as {33, 32, 27, 22, 20, 23, 27, 30, 34, 31}, or as {27.9}. In some embodiments, the sensor-individual correlator could be determined at least in part from the environmental measurements.

In the depicted embodiment, RF location tag 202 transmits a tag signal to receiver 106 and sensor 203 transmits a sensor signal to sensor receiver 166. The sensor signal may comprise one or more sensor information packets. Such sensor information packets may include any data or information from the sensor 203 that is intended for transmission such as, for example in the depicted embodiment, sensor UID, additional stored sensor data, sensor-individual correlator, and environmental measurements. A receiver signal from receiver 106 and a sensor receiver signal from sensor receiver 166 may be transmitted via wired or wireless communication to receiver hub/locate engine 108 as shown.

FIG. 3C depicts a sensor 203 communicating through a RF location tag 202 in accordance with various embodiments. In one embodiment, the sensor 203 may be part of (i.e., reside in the same housing or assembly structure) of the RF location tag 202. In another embodiment, the sensor 203 may be distinct from (i.e., not resident in the same housing or assembly structure) the RF location tag 202 but configured to communicate wirelessly or via wired communication with the RF location tag 202.

In one embodiment, the RF location tag 202, the sensor 203, or both, may generate and/or store a tag-sensor correlator that indicates an association between a RF location tag 202 and a sensor 203 (e.g., tag UID/sensor UID, distance from tag to sensor in a particular stance, set of sensors associated with a set of tags, sensor types associated with a tag, etc.). In the depicted embodiment, both the RF location tag 202 and the sensor 203 store the tag-sensor correlator.

In the depicted embodiment, sensor 203 transmits a sensor signal to RF location tag 202. The sensor signal may comprise one or more sensor information packets as discussed above. The sensor information packets may comprise the sensor UID, a sensor-individual correlator, additional stored sensor data, the tag-sensor correlator, and/or the environmental measurements. The RF location tag 202 may store some portion of, or all of, the sensor information packets locally and may package the sensor information packets into one or more tag data packets for transmission to receiver 106 as part of a tag signal or simply pass them along as part of its tag signal.

Figures 3D, 3E:
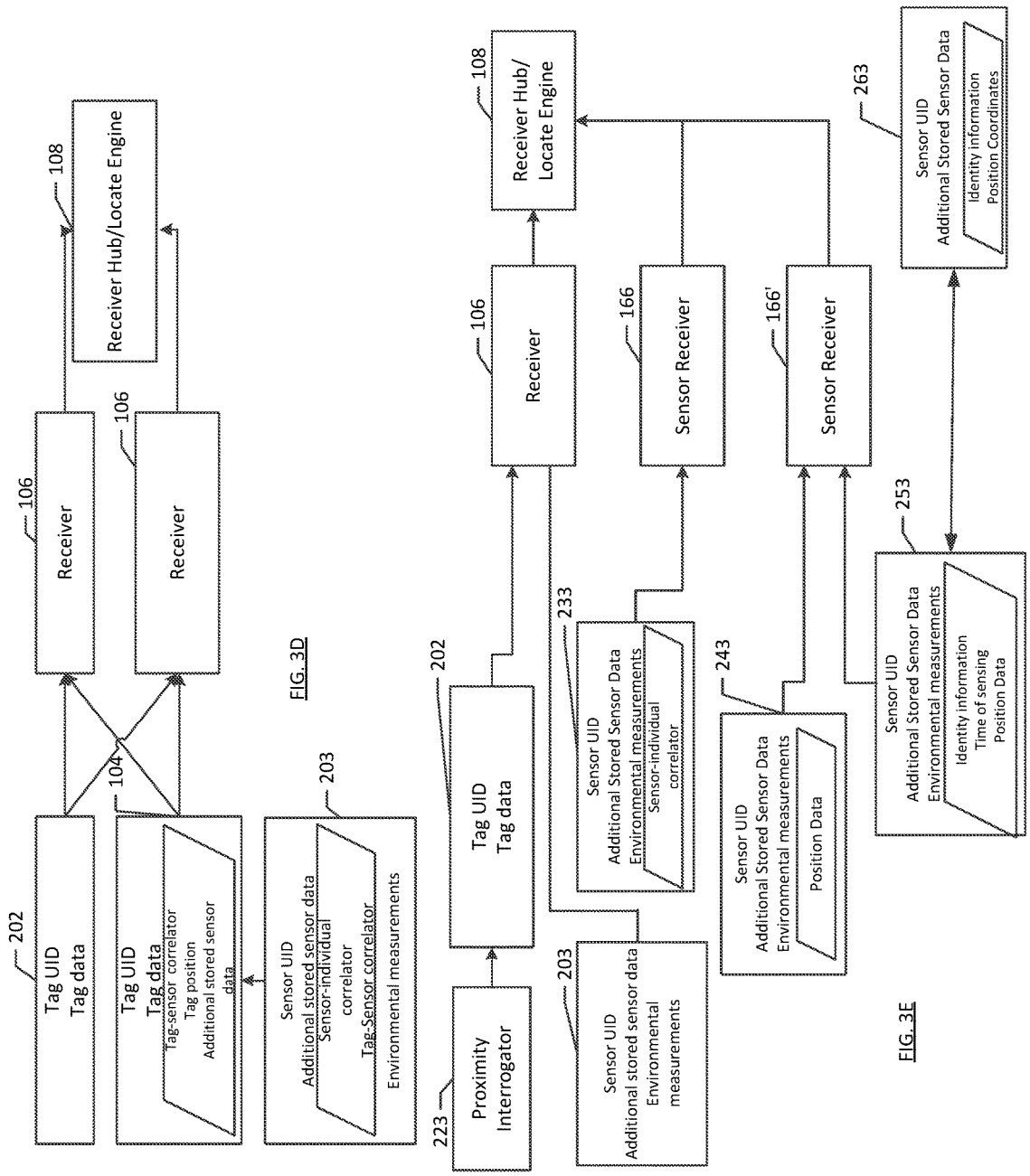

FIG. 3D illustrates an example communication structure for a reference tag 104 (e.g., reference tag 104 of FIG. 1), an RF location tag 202, a sensor 203, and two receivers 106 in accordance with one embodiment. The depicted reference tag 104 is a RF location tag and thus may include tag data, a tag UID, and is capable of transmitting tag data packets. In some embodiments, the reference tag 104 may form part of a sensor and may thus be capable of transmitting sensor information packets.

The depicted sensor 203 transmits a sensor signal to RF reference tag 104. The RF reference tag 104 may store some portion or some or all of the sensor information packets locally and may package the sensor information packets into one or more tag data packets for transmission to receiver 106 as part of a tag signal, or simply pass them along as part of its tag signal.

As was described above in connection with FIG. 1, the receivers 106 of FIG. 3D are configured to receive tag signals from the RF location tag 202 and the reference tag 104. Each of these tag signals may include blink data, which may comprise tag UIDs, tag data packets, and/or sensor information packets. The receivers 106 each transmit receiver signals via wired or wireless communication to the receiver hub/locate engine 108 as shown.

FIG. 3E illustrates an example communication structure between an RF location tag 202, a plurality of receivers 106, and a variety of sensor types including, without limitation, a sensor 203, a diagnostic device 233, a triangulation positioner 243, a proximity positioner 253, and a proximity label 263 in accordance with various embodiments. In the depicted embodiment, none of the sensors 203, 233, 243, 253 form part of an RF location tag 202 or reference tag 104. However, each may comprise a sensor UID and additional stored sensor data. Each of the depicted sensors 203, 233, 243, 253 transmits sensor signals comprising sensor information packets.

In the depicted embodiment, receiver 106 is configured to receive a tag signal from RF location tag 202 and a sensor signal directly from sensor 203. In such embodiments, sensor 203 may be configured to communicate in a communication protocol that is common to RF location tag 202 as will be apparent to one of ordinary skill in the art in view of this disclosure.

FIG. 3E depicts one type of sensor referred to herein as a "proximity interrogator". The proximity interrogator 223 can include circuitry operative to generate a magnetic, electromagnetic, or other field that is detectable by a RF location tag 202. While not shown in FIG. 3E, a proximity interrogator 223 may include a sensor UID and other tag and sensor derived data or information as discussed above.

In some embodiments, the proximity interrogator 223 is operative as a proximity communication device that can trigger a RF location tag 202 (e.g., when the RF location tag 202 detects the field produced by the proximity interrogator 223) to transmit blink data under an alternate blink pattern or blink rate. The RF location tag can initiate a preprogrammed (and typically faster) blink rate to allow more location points for tracking an individual. In some embodiments, the RF location tag may not transmit a tag signal until triggered by the proximity interrogator 223. In some embodiments the RF location tag 202 may be triggered when the RF location tag 202 moves near (e.g., within communication proximity to) a proximity interrogator 223. In some embodiments, the RF location tag may be triggered when the proximity interrogator 223 moves near to the RF location tag 202.

In other embodiments, the RF location tag 202 may be triggered when a button is pressed or a switch is activated on the proximity interrogator 223 or on the RF location tag itself. For example, a proximity interrogator 223 could be placed at the start line of a racetrack. Every time a car passes the start line, a car-mounted RF location tag 202 senses the signal from the proximity interrogator and is triggered to transmit a tag signal indicating that a lap has been completed. As another example, a proximity interrogator 223 could be placed at a Gatorade cooler. Each time a player or other participant fills a cup from the cooler a participant-mounted RF location tag 202 senses the signal from the proximity interrogator and is triggered to transmit a tag signal indicating that Gatorade has been consumed. As another example, a proximity interrogator 223 could be placed on a medical cart. When paramedics use the medical cart to pick up a participant (e.g., a player) and move him/her to the locker room, a participant-mounted RF location tag 202 senses the signal from the proximity interrogator and is triggered to transmit a tag signal indicating that they have been removed from the game. As explained, any of these post-triggered tag signals may differ from pre-triggered tag signals in terms of any aspect of the analog and/or digital attributes of the transmitted tag signal.

FIG. 3E depicts another type of sensor that is generally not worn by an individual but is referred to herein as a "diagnostic device". However, like other sensors, diagnostic devices may measure one or more environmental conditions and store corresponding environmental measurements in analog or digital form.

While the depicted diagnostic device 233 is not worn by an individual, it may generate and store a sensor-individual correlator for association with environmental measurements taken in connection with a specific individual. For example, in one embodiment, the diagnostic device 233 may be a blood pressure meter that is configured to store as environmental measurements blood pressure data for various individuals. Each set of environmental measurements (e.g., blood pressure data) may be stored and associated with a sensor-individual correlator.

The depicted diagnostic device 233 is configured to transmit a sensor signal comprising sensor information packets to a sensor receiver 166. The sensor information packets may comprise one or more of the sensor UID, the additional stored data, the environmental measurements, and/or the sensor-individual correlator as discussed above. The sensor receiver 166 may associate some or all of the data from the sensor information packets with other stored data in the sensor receiver 166 or with data stored or received from other sensors, diagnostic devices, RF location tags 102, or reference tags. The sensor receiver 166 transmits a sensor receiver signal to a receiver hub/locate engine 108.

Another type of sensor shown in FIG. 3E is a triangulation positioner 243. A "triangulation positioner" is a type of sensor that senses position. The depicted triangulation positioner 243 includes a sensor UID, additional stored sensor data, and environmental measurements as discussed above.

In some embodiments, a triangulation positioner (also known as a global positioning system (GPS) receiver) receives clock data transmitted by one or more geostationary satellites (a satellite in a known or knowable position) and/or one or more ground based transmitters (also in known or knowable positions), compares the received clock data, and computes a "position calculation". The position calculation may be included in one or more sensor information packets as environmental measurements.

In another embodiment, a triangulation positioner comprises one or more cameras or image-analyzers that receive emitted or reflected light or heat, and then analyzes the received images to determine the location of an individual or sensor. Although a triangulation positioner may transmit data wirelessly, it is not a RF location tag because it does not transmit blink data or a tag signal that can be used by a receiver hub/locate engine 108 to calculate location. In contrast, a triangulation positioner senses position and computes a position calculation that may then be used as environmental measurements by the receiver hub/locate engine 108.

In one embodiment, a triangulation positioner could be combined with a RF location tag or reference tag (not shown). In such embodiments, the triangulation positioner could compute and transmit its position calculation via the RF location tag to one or more receivers. However, the receiver hub/locate engine would calculate tag location based on the blink data received as part of the tag signal and not based solely on the position calculation. The position calculation would be considered as environmental measurements and may be included in associated sensor information packets.

As will be apparent to one of ordinary skill in the art, position calculations (e.g., GPS receiver position calculations) are not as accurate as the location calculations (e.g., UWB waveform based location calculations) performed by receiver hub/locate engines structured in accordance with various embodiments of the invention. That is not to say that position calculations may not be improved using known techniques. For example, a number of influences, including atmospheric conditions, can cause GPS accuracy to vary over time. One way to control this is to use a differential global positioning system (DGPS) comprising one or a network of stationary triangulation positioners that are placed in a known position, and the coordinates of the known position are stored in memory as additional stored sensor data. These triangulation positioners receive clock data from geostationary satellites, determine a position calculation, and broadcast a difference between the position calculation and the stored coordinates. This DGPS correction signal can be used to correct for these influences and significantly reduce location estimate error.

Another type of sensor shown in FIG. 3E is a proximity detector 253. A "proximity detector" is a type of sensor that senses identity within an area (e.g., a local area) that is small with respect to the monitored area 100 of FIG. 1. Many different ways of sensing identity (e.g., a unique ID or other identifier for a sensed object or individual) would be apparent to one of ordinary skill in the art in view of this disclosure including, without limitation, reading a linear bar code, reading a two-dimensional bar code, reading a near field communication (NFC) tag, reading a RFID tag such as a UHF tag, HF tag, or low frequency tag, an optical character recognition device, a biometric scanner, or a facial recognition system.

In some embodiments, a proximity detector senses an attribute of an individual (or an individual's wristband, tag, label, card, badge, clothing, uniform, costume, phone, ticket, etc.). The identity sensed by a proximity detector may be stored locally at the proximity detector 253 as shown and transmitted as environmental measurements via one or more sensor information packets to a sensor receiver 166.

In some embodiments, a proximity detector 253 may have a defined position, which is often stationary, and may be associated with a location in the monitored area 100 of FIG. 1. For example, a proximity detector 253 could be located at a finish line of a race track, an entrance gate of a stadium, with a diagnostic device, at a goal line or goal post of a football field, at a base or home plate of a baseball diamond, or a similar fixed location. In such embodiments where the proximity detector is stationary, the position coordinates of the proximity detector and a sensor UID could be stored to a monitored area database (not shown) that is accessible by one or more of the receivers 106, 166, the receiver hub/locate engine 108, and/or other components of the central processor/hub 108. In embodiments where the proximity detector is movable, a position calculation could be determined with a triangulation positioner, or the proximity detector could be combined with a RF location tag and located by the receiver hub/locate engine 108. While shown as separate fields for illustration purposes in FIG. 3E, identify information and position calculation could comprise part of the additional stored sensor data, the environmental measurements, or both.

In one embodiment, the proximity detector could be associated with a reference tag (e.g., tag 104 of FIG. 1) whose position is recorded in the monitored area database. In other embodiments, the proximity detector is movable, such that it may be transported to where it is needed. For example, a proximity detector 253 could be located on a medical cart, first down marker, a diagnostic device, goal post, or carried by a paramedic or security guard. In an embodiment where the proximity detector 253 is movable it would typically be associated with a RF location tag or triangulation positioner so that location (for a RF location tag) or position (for a triangulation positioner) can be determined at the time identity is sensed.

In the embodiment where the proximity detector includes a RF location tag, the receiver hub/locate engine 108 would locate the associated RF location tag, and the tag data/sensor data filter 112 would associate the tag location data for the associated RF location tag as the position of the proximity detector, while determining the identity of an associated individual from any received sensor information packets. In the alternate embodiment where the proximity detector includes a triangulation positioner, the triangulation positioner would compute a position calculation that could be stored as additional stored sensor data and/or environmental measurements, and transmitted as one or more sensor information packets. In one embodiment, sensor information packets for a proximity detector may include both sensed identity information and a position calculation.

Another type of sensor shown in FIG. 3E is a proximity label 263. A proximity label has a fixed position and an identification code (e.g., a sensor UID). The proximity label 263 may further comprise additional stored sensor data as shown. The depicted proximity label 263 is configured to be read by proximity detector 253. In some embodiments, proximity detector 253 may be further configured to write information to proximity label 263.

A proximity label 263 may be a sticker, card, tag, passive RFID tag, active RFID tag, NFC tag, ticket, metal plate, electronic display, electronic paper, inked surface, sundial, or otherwise visible or machine readable identification device as is known in the art. The coordinates of the position of the proximity label 263 are stored such that they are accessible to the receive hub/locate engine 108. For example, in one embodiment, the position coordinates of a proximity label 263 could be stored in a field database or monitored area database accessible via a network, or stored locally as additional stored data in the proximity detector 253.

In some embodiments, a position of the proximity label 263 is encoded into the proximity label 263 itself. For example, coordinates of a position of the proximity label 263 could be encoded into a passive RFID tag that is placed in that position. As another example, the coordinates of a position of the proximity label 263 could be encoded into a printed barcode that is placed in that position. As another example, a proximity label 263 comprising a NFC tag could be encoded with the location "end zone", and the NFC tag could be placed at or near an end zone at Bank of America stadium. In some embodiments, the stored coordinates of the proximity label 263 may be offset from the actual coordinates of the proximity label 263 by a known or determinable amount.

In one embodiment, a proximity label 263 such as an NFC tag may be encoded with a position. When a sensor such as a proximity detector approaches the NFC tag it may read the position, then transmit the position in a sensor information packet to the sensor receiver 166' and eventually to the receiver hub/locate engine 108. In another embodiment, a proximity label 263 such as a barcode label may be encoded with an identification code. When a smartphone with a proximity detector (such as a barcode imager) and a triangulation positioner (such as a GPS chip, GPS application, or similar device) approaches the barcode label it may read the identification code from the barcode, determine a position calculation from received clock data, then transmit the identity and the position calculation to sensor receiver 166' and eventually to the receiver hub/locate engine 106 as part of one or more sensor information packets.

In the depicted embodiment, triangulation positioner 243 and proximity detector 253 are each configured to transmit sensor signals carrying sensor information packets to sensor receiver 166'. The depicted sensors 243, 253, like any sensor discussed herein, may transmit sensor signals via wired or wireless communication protocols. For example, any proprietary or standard wireless protocol (e.g., 802.11, Zigbee, ISO/IEC 802.15.4, ISO/IEC 18000, IrDA, Bluetooth, CDMA, or any other protocol) could be used for the sensor signals. Alternatively or additionally, any standard or proprietary wired communication protocol (e.g., Ethernet, Parallel, Serial, RS-232, RS-422, USB, Firewire, I2C, etc.) may be used. Similarly, sensor receiver 166', and any receiver discussed herein, may use similar wired and wireless protocols to transmit receiver signals to the receiver hub/locate engine.

In one embodiment, upon receiving sensor signals from the triangulation positioner 243 and the proximity detector 253, the sensor receiver 166' may associate some or all of the data from the received sensor information packets with other data stored to the sensor receiver 166', or with data stored or received from other sensors (e.g., sensor 203), diagnostic devices 233, RF location tags 102, or RF reference tags 104. Such associated data is referred to herein as "associated sensor data". In the depicted embodiment, the sensor receiver 166' is configured to transmit some or all of the received sensor information packets and any associated sensor data to the receiver hub/locate engine 108 at part of a sensor receiver signal.

In one embodiment, a smartphone comprising a proximity detector (such as a barcode imager) and a triangulation positioner (such as a GPS chip) may associate an identification code determined from a barcode with a position calculation from received clock data as associated sensor data and transmit a sensor information packet that includes such associated sensor data to the receiver hub/locate engine 108. In another embodiment, the smartphone could transmit a first sensor information packet including the identification code and the smartphone's unique identifier to another sensor receiver, the smartphone could transmit a second sensor information packet including the position calculation and the smartphone's unique identifier to the sensor receiver, and the sensor receiver could associate the position calculation with the identification code based on the common smartphone unique identifier and transmit such associated sensor data to the receiver hub/locate engine 108. In another embodiment, the sensor receiver could determine a first time measurement associated with the first sensor information packet and a second time measurement associated with the second sensor information packet that, in conjunction with the sensor UID, could be used, by the receiver hub/locate engine 108, to associate the first sensor information packet with the second sensor information packet.

In one embodiment, the receiver hub/locate engine 108 receives receiver signals from the receiver 106 and sensor receiver signals from the sensor receivers 166, 166'. In the depicted embodiment, receiver 106 may receive blink data from the RF location tag 102 and transmits to the receiver hub/locate engine 108 some or all of the blink data, perhaps with additional time measurements or signal measurements. In some embodiments, time measurements or signal measurements may be based on a tag signal received from a RF reference tag (e.g., reference tag 104 of FIG. 1). The receiver hub/locate engine 108 collects the blink data, time measurements (e.g. time of arrival, time difference of arrival, phase), and/or signal measurements (e. g. signal strength, signal direction, signal polarization, signal phase) from the receivers 106 and computes tag location data for the tags 102 as discussed above in connection with FIG. 1. In some embodiments, the receivers 106 may be configured with appropriate RF filters, such as to filter out potentially interfering signals or reflections proximate the field of play or other area to be monitored.

The receiver hub/locate engine 108 may also access stored data or clock data from local storage and from a network location. The receiver hub/locate engine 108 uses this information to determine tag location data for each RF location tag. It may also associate data derived or extracted from tag signals transmitted from one or more RF location tags with information or data derived or extracted from sensor signals transmitted from one or more sensors.

In addition to the TOA or TDOA systems previously described, other real-time location systems (RTLS) such as received signal strength indication based systems could potentially be implemented by a receiver hub/locate engine 108. Any RTLS system using RF location tags, including those described herein, could require considerable processing by the receiver hub/locate engine 108 to determine the tag location data from the blink data received from the tags. These may require time measurement and/or signal measurement in addition to blink data, which preferably includes a tag UID. In contrast, in other systems, such as global position systems (GPS) systems, location data is determined based upon the position calculation transmitted from a GPS transmitter (also referred to as a GPS receiver or GPS tag) which includes calculated information about the location where the tag was positioned (i.e., coordinates determined at the tag via satellite signal triangulation, etc.) when the position calculation was determined or stored. Thus, GPS information typically refers to additional information that is transmitted along with a GPS transmitter ID before the transmission is received by a sensor receiver.

A GPS host device or back-end server may receive the GPS information and simply parse the position calculation (as opposed to calculating the position information at the host device) and the GPS transmitter ID into a data record. This data record may be used as a GPS position calculation, or it could be converted to a different coordinate system to be used as a GPS position calculation, or it could be processed further with DGPS information to be used as a GPS position calculation.

Returning to FIG. 3C, the depicted RF location tag 202 is used to convey (sometimes called backhaul) sensor information packets to a receiver 106. In some embodiments, while not shown, multiple sensors 203 may transmit sensor signals carrying sensor information packets to RF location tag 202. Such received sensor information packets may be associated with blink data that is transmitted to receiver 106.

In one embodiment, the receiver hub/locate engine 108 may parse sensor information packets from received tag data packets and associate such sensor information packets with the RF location tag 202 that transmitted the sensor information packet. Thus, the receiver hub/locate engine 108 may be able to determine tag location data, which may comprise a location and other data (e.g., tag data, tag UID, tag-individual correlator, sensor-individual correlator, additional stored sensor data, environmental measurements, tag-sensor correlator, identity information, position calculation, etc.) from one or more tags or sensors. Such data and information may be transmitted to the central processor/hub 108.

In some embodiments, once the receiver hub/locate engine 108 determines a location estimate of a RF location tag 102 at the time epoch of the tag signal, the receiver hub/locate engine 108 can also associate a location estimate with the tag data packet included in the blink data of such tag signal. In some embodiments, the location estimate of the tag signal may be used as tag location data for the tag data packet. In some embodiments a Geographical Information System (GIS) may be used by the receive hub/locate engine 108 to refine a location estimate, or to map a location estimate in one coordinate system to a location estimate in a different coordinate system, to provide a location estimate for the tag data packet.

In one embodiment, the location estimated for the tag data packet may be associated with any data in the tag data packet, including a tag UID, other tag data, and, if included, one or more sensor information packets, including sensor UID, additional stored sensor data, and environmental measurements. Since environmental measurements may include a position calculation from a triangulation positioner (e.g., a GPS device), the receiver hub/locate engine 108 could parse the position calculation and use it to refine a location estimate for the tag data packet.

Preferably, the receiver hub/locate engine 108 may access an individual database to determine tag-individual correlators or sensor-individual correlators. Individual data (e.g., an individual profile) may be stored in a server, in tag memory, in sensor memory, or in other storage accessible via a network or communication system, including tag data or additional stored sensor data as explained previously.

In some embodiments, by comparing data accessed using a sensor-individual correlator, the receiver hub/locate engine 108 may associate an individual with a sensor information packet received from a sensor, and/or may associate an individual with such sensor. Because the receiver hub/locate engine 108 may associate a sensor position estimate with a sensor information packet, the receiver hub/locate engine 108 may also estimate an individual position for the associated individual.

In another embodiment, by comparing data accessed using a tag-sensor correlator, the receiver hub/locate engine 108 may associate a sensor with a tag data packet received from a RF location tag 102. Because the receiver hub/locate engine 108 may associate a location estimate with a tag data packet, the receiver hub/locate engine 108 may also create a sensor location estimate for the associated sensor. By comparing a location estimate for a RF location tag with a sensor location estimate or a sensor position estimate, the receiver hub/locate engine 108 may associate a RF location tag with a sensor, or may associate a tag data packet with a sensor information packet. The receiver hub/locate engine 108 could also determine a new or refined tag-sensor correlator based on this association.

In still another embodiment, by comparing a location estimate for a RF location tag with an individual location estimate or an individual position estimate, the receiver hub/locate engine 108 may associate a RF location tag with an individual, or may associate a tag data packet with an individual. The receiver hub/locate engine 108 could also determine a new or refined tag-individual correlator based on this association.

In one embodiment, by comparing a location estimate for a sensor with an individual location estimate or an individual position estimate, the receiver hub/locate engine 108 may associate a sensor with an individual, or may associate a sensor information packet with an individual. The receiver hub/locate engine 108 could also determine a new or refined sensor-individual correlator based on this association.

Data derived or extracted from tag signals transmitted from one or more RF location tags is referred to herein as "tag derived data" and shall include, without limitation, tag data, tag UID, tag-individual correlator, tag-sensor correlator, tag data packets, blink data, time measurements (e.g. time of arrival, time difference of arrival, phase), signal measurements (e.g., signal strength, signal direction, signal polarization, signal phase) and tag location data (e.g., including tag location estimates). Tag derived data is not derived by the RF location tag, but rather, is derived from information transmitted by the RF location tag. Information or data derived or extracted from sensor signals transmitted from one or more sensors is referred to herein as "sensor derived data" and shall include, without limitation, sensor UID, additional stored sensor data, sensor-individual correlator, environmental measurements, sensor information packets, position calculations (including sensor position estimates), position information, identity information, tag-sensor correlator, and associated sensor data. Data derived or extracted from stored individual data is referred to herein as "individual profile information", "participant profile information", or simply "profile information" and shall include, without limitation tag-individual correlator, sensor-individual correlator, identity information, name, uniform number and team, biometric data, tag position on individual. In various embodiments, the receiver hub/locate engine 108 may transmit tag derived data, sensor derived data, individual profile information, various combinations thereof, and/or any information from the GIS, the field database, the monitored area database, and the individual database to the central processor/hub 108.

Example Receiver Hub and Receiver Processing and Distribution System

Figure 4:
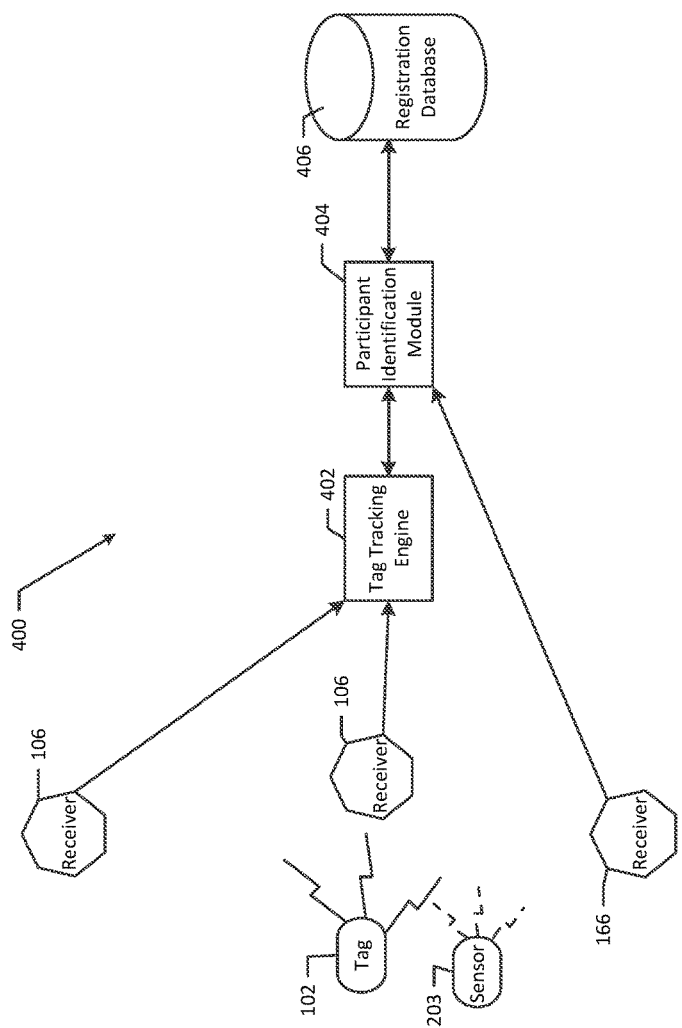
FIG. 4 illustrates an exemplary system for associating tags with participants in accordance with some embodiments of the present invention.

FIG. 4 illustrates an exemplary system 400 for associating a tag and/or sensor 203 with a participant in accordance with some embodiments of the present invention. The depicted system 400 may be distributed across a receiver hub 108 and a central processor/hub 108 of the type depicted in FIG. 1. In alternative embodiments, the system 400 may be housed or located in a single housing or unit. In still further embodiments, the system 400 may be distributed among multiple additional housings or units depending upon the application and other design parameters that will be apparent to one of ordinary skill in the art in view of this disclosure.

The system 400 of FIG. 4 may include a plurality of tags 102, and sensors 203, associated with participants (e.g., players, officials, balls, field markers, etc.), a plurality of receivers 106 and/or sensor receivers 166 within a monitored environment, a tag tracking engine 402, a participant identification module 404, and a database of tag registrations 406.

In an exemplary system 400, such as illustrated in FIG. 4, the plurality of tags 102 (and sensors 203) may be attached to a participant as discussed in connection with FIGS. 3A-E. In some embodiments, the plurality of tags 102 may be activated and deactivated as needed, such as before and after a game or when damaged or to replace batteries, power supplies, local memory, etc. Each of the tags 102 may transmit data, including a unique ID and other tag derived data, which is received by one or more of the receivers 106. In some embodiments, the receivers 106 may be configured with appropriate RF filters, such as to filter out potentially interfering signals or reflections proximate the field of play or other environment to be monitored.

Each of the receivers 106 may receive tag signals transmitted from the tags 102 and transmit tag derived data to the tag tracking engine 402. In the depicted embodiment, a sensor receiver 166 receives sensor signals transmitted from the sensors 203 and transmits sensor derived data to a participant identification module 404. The tag tracking engine 402 may collect the tag derived data from the receivers 106 and compute tag location data for the tags 102 as discussed above in connection with FIG. 1. The tag location data may then be provided to the participant identification module 404 that may use the tag location data and, optionally, received sensor derived data, to associate a particular tag and/or sensor with a particular participant.

Associations between the tags 102, sensors 203 and particular participants may be stored within a registration database 406. The registration database 406 may include a list of unique identifiers for the particular tags and/or sensors and information indicating which tags/sensors is associated with which participant. For example, the registration database 406 may include data linking a particular set of tags with a particular player (e.g., tag-individual correlators), a particular piece of player equipment (e.g., tag-equipment correlators), a particular game ball (e.g., tag-ball correlators), a particular sensor (e.g., tag-sensor correlators) or the like. The registration database 406 may further include data linking a particular set of sensors with a particular player (e.g., sensor-individual correlators), a particular piece of player equipment (e.g., sensor-equipment correlators), a particular game ball (e.g., sensor-ball correlators), a particular tag (e.g., tag-sensor correlators) or the like. The registration database 406 may further include participant data, profile data, and/or role data for participants that are registered with each tag or tags, and vice-versa.

The registration database 406 may be populated with the association for each tag and/or sensor at the time the tag/sensor is registered and/or activated for the particular participant. Tags/sensors may also be re-associated or reallocated as needed. For example, a malfunctioning tag may be replaced during a game with a replacement tag. Embodiments may function to associate the replacement tag with the same participant from which the malfunctioning tag was removed. Embodiments may further function to associate the replacement tag with one or more sensors that were previously associated with the replaced or original tag.

The registration database 406 may further include descriptors for each tag. For example, a given tag associated with the left side of a player's shoulder pads may be associated with a "shoulder-left" descriptor, and a tag associated with the right side of the player's shoulder pads may be associated with a "shoulder-right" descriptor. These descriptors may be utilized to identify each tag with a particular spatial or physical location on the participant. In one embodiment, the descriptor may include a set of coordinates relative to the participant while in a particular stance, such that a tag on the right foot might be 0 cm, 3 cm, 0 cm; a tag on the right shoulder might be 0 cm, 150 cm, 2 cm; a tag on the right wrist might be −65 cm, 150 cm, 0 cm. In some embodiments, one of the tags may be at position 0,0,0 and other tags associated with the participant would be at positions relative to the first tag. One skilled in the art would see that non-Cartesian coordinate systems could be used. In some embodiments, two tags on the same participant may be in fixed positions relative to each other, such as the left and right shoulder, or back and front. In some embodiments two tags on the same participant may be in variable positions relative to each other, such as a hand and foot, which may vary relative to each other based on stance or body movement. The registration database may include information related to whether the position of the tag is fixed or variable relative to the coordinate system, a physical feature of the participant, or a particular tag associated with the participant.

In some embodiments, the registration database 406 may further include a tag association model for each participant type. The tag association model may include a list of expected tags and/or sensors for association with each participant. For example, a player may be associated with four tags, one located in each side of their shoulder pads and one in each knee pad, while a ball or penalty flag might be associated with a single tag. The tag association model for each participant may define how many tags are expected to be associated with that participant. In some embodiments, the model may further include spatial information about the location or orientation of the tags for each participant with respect to one another. For example, a "player" spatial model might include four tags representing tags located on each shoulder and each knee. These spatial model may include information specifying an expected distance range between each of the tags, such as "18-36 inches" for the shoulder tags and "6-48 inches" for each of the knee tags. Similarly, the spatial model may indicate expected locations in a three dimensional plane for each set of tags, such as by indicating that shoulder tags are generally expected to be located physically above knee tags.

Such models may be employed to assist with the registration of unknown tags. For example, if a model indicates that each player should be registered with 4 tags, but a given player is only associated with 3 tags and the system identifies one unregistered tag, then the system may determine to register the unregistered tag with the player who is missing a tag. The location of the unregistered tag in relation to the location of the other three tags associated with the player may be utilized to determine whether the unregistered tag is likely to be a correct association for the player. For example, if the unregistered tag is located more than 10 yards from the player missing a tag, then the system may choose not to register the unregistered tag with the player missing the tag. Similarly, if the system determines that an unregistered tag does not conform with the spatial model for a given player (e.g., the unregistered tag's location would be physically impossible on a human being given the relative locations of the registered tags), the system may also not register the tag with the player or may instead flag an error condition for a technician to investigate.

In some embodiments, tag association models may be employed to perform error checking of data received from location tags. In some scenarios, a signal reflection or interference may result in one or more tags reading inaccurate locations. A tag association model may be employed to compare data received from other tags associated with the participant to identify outliers or possible erroneous data. For example, if one tag of four tags associated with a given participant registers a location much farther away than the other three tags associated with the participant, then the location information from the first tag may be flagged as possibly erroneous and possibly filtered out. In response to multiple such location readings, the tag may be flagged as malfunctioning and deactivated, and/or a technician may be notified automatically to investigate and replace the tag. An example of a process for using such models to detect erroneous data is described below with respect to FIG. 11.

In some embodiments, data from one or more of the sensors (e.g., a proximity detector, proximity label, etc.) is used to determine the association between a particular tag and a particular participant. The participant identification module 404 may receive the sensor derived data and data from the tag tracking engine to determine correlations between the identity of the participant and an identifier associated with the tag. Upon determining this correlation, an entry for the particular tag-participant association (e.g., a tag-individual correlator) may be created within the tag registration database 406. Tag derived data for registered tags may be used to assist with the registration of unregistered tags, such as described above with respect to the models and below with respect to FIGS. 5-10.

The foregoing description describes various example techniques for determining participant associations for one or more unassociated or unallocated RF location tags. While not discussed in detail below to avoid duplication, it will be readily apparent to one of ordinary skill in the art that the inventive concepts described below may also be applied to determining participant or tag associations for one or more unassociated or unallocated sensors.

Example proximity detectors and proximity labels that may be used for determining these tag associations may include camera sensors, biometric sensors, bar code readers, RFID readers, other RFID tags, or the like. As an example, embodiments may include the ability to determine a location of an unallocated tag. For example, the tag tracking engine 402 may detect the presence of a tag not associated with any particular participant (e.g., in the case of an unassociated replacement tag). The tag tracking engine 402 may be operable to identify the location of the unassociated tag, and to direct a camera sensor (e.g., a proximity detector) to view the location of the unassociated tag. The camera sensor may be employed to detect the presence of one or more participants at the location of the unassociated tag, and the participant identification module may be operable to determine the participant to be associated with the unassociated tag based on which participants are present (e.g., if it can be determined that all of the visible participants at the location but one have all of their associated tags accounted for, then the participant identification module 404 may associate the unassociated tag with the one participant with an unaccounted-for tag).

As another example embodiment, the proximity detectors may include biometric sensors. For example, upon replacing a tag a participant may provide biometric data via a fingerprint reader, retinal scanner, facial recognition scanner, or the like. The biometric data may be provided to the participant identification module 404 to determine the identity of the participant. For example, the participant identification module 404 may access a biometric database (not pictured) containing biometric data for a particular set of participants. The biometric data may be matched to a particular participant. The biometric scanner may further send an identifier for the particular tag to be associated with the particular participant to the participant identification module 404, such as via a wireless network connection, and the particular tag identifier may be associated with the particular participant within the registration database 406.

As yet another example embodiment, the locations of two or more proximity detectors, receivers 106, or sensor receivers 166 may be used to correlate a tag or sensor to a participant. For example, participants may enter a field or zone in a particular order (e.g., players leaving the locker room in a single file manner via a tunnel), and the order may be known to the system. A receiver 106 (or optionally a proximity detector or sensor receiver 166) may be strategically placed to read tags (or sensors) affixed to each participant as they pass by the receiver in the particular order, such that the participant identification module 404 associates the tags or sensor with the particular participants in the order in which the tags or sensors are read.

In yet further embodiments, a sensor 204 or, more specifically, a proximity detector may be a device used to configure tags for use by participants. For example, the sensor 204 may be a handheld or mobile device employed by a user to provide data to the participant identification module 404 indicating that a particular tag should be registered with a particular participant. The mobile device may provide the ability to transmit identification data (e.g., sensor derived data, identify information, time of sensing, etc.) to the participant identification module when a tag is replaced. The mobile device may provide the capability to indicate which tag for which user is being replaced (e.g., left shoulder pad tag for player A, or right knee tag for player B), and an identifier (e.g., tag UID) associated with the tag that is being replaced. The identifier associated with a tag may be transmitted via an RF signal by the tag, or displayed on the tag, possibly as text or a bar code; one skilled in the art would appreciate that the UID transmitted by the tag could be the same or different as that displayed on the tag, providing that there was sufficient information to correlate the identification data (tag UID or environmental measurements) captured by the mobile device with the UID transmitted by the tag in blink data. In some embodiments, the mobile device may be functional to receive environmental measurements, such as biometric data as described above, and transmit the environmental measurements to the participant identification module 404 for use in associating the tag with the particular participant.

In some examples, the mobile device make take the form of a DartWand™ that is operable to configure one or more tags at distances up to 60 cm and detect tag emissions up to 150 m. An exemplary DartWand™ manufactured by Zebra Technologies is the Zebra DartWand™ Module, a small table top device used to configure and inventory DartTags™ that turns tags on and off and sets their blink rate to one of a wide range of rates.

In yet further embodiments, the participant identification module 404 may associate a particular tag with a particular participant by monitoring the tag location received from the tag tracking engine 402, and deriving the identity of the participant based on the locations of the other tags in relation to the particular tag. For example, the participant identification module 404 may determine that a particular unassociated tag is consistently present in proximity to a set of assigned tags corresponding to a particular participant, and thus it may be appropriate to associate the unassociated tag with the particular participant. In this way, for example, a replacement tag located on equipment worn by a participant could be automatically associated with the participant based on the replacement tags consistent proximity to other tags worn by the participant. Embodiments may further utilize the techniques described above with respect to determining which players are "missing" tags to assist with determining the appropriate participant for assignment.

In yet further embodiments, the participant identification module 404 may associate a particular tag with a particular participant based on a unique signal received from the participant or equipment associated with a participant. In a first example, a proximity label, e.g., a passive RFID label, may be stitched or otherwise attached to a jersey or other identifying piece of equipment associated with a participant, the passive RFID label being configured to identify the identifying piece of equipment, such as the jersey number, when read by a proximity detector or other sensor, such as a RFID reader.

In yet further embodiments, the participant identification module 404 may associate a particular tag with a particular participant based on an identifying number included as part of tag derived data (e.g., a tag UID, tag-individual correlator, or a variable field) in some or all transmitted tag signals. In some embodiments, such an identifying number transmission may be transmitted in a first transmitted tag signal from a particular tag.

Figure 5A:
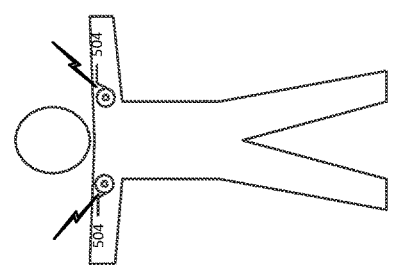

FIGS. 5A-D illustrate an exemplary tag activation process with respect to a participant in accordance with some example embodiments of the present invention. As described above, tags may begin to provide location information to a RTLS system in response to an activation signal. FIG. 5A illustrates a player with two deactivated tags 502 on the player's shoulders (e.g., embedded within the player's shoulder pad equipment). These tags are activated in FIG. 5B, where they are displayed as activated tags 504 that are capable of transmitting blink data in a RTLS system.

Figure 5C:
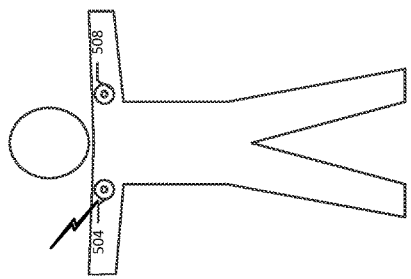
Figure 5B:
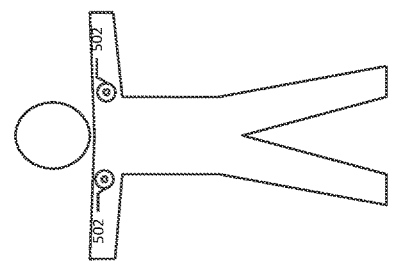
Figure 5D:
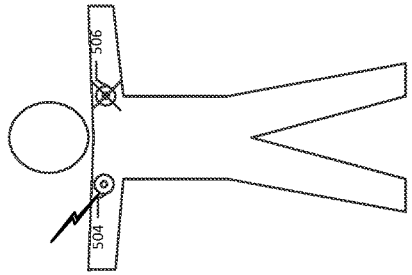

FIG. 5C illustrates a scenario in which one of the tags 506 has become damaged or otherwise malfunctioned. The malfunctioning tag 506 may cease providing location information. Various methods of malfunctioning may occur. For example, a tag power source (e.g., a battery) may be depleted, the tag 506 may have suffered physical damage, or the tag 506 may have been misplaced, or the tag 506 may have become obscured by mud, Gatorade, or some other RF shielding foreign substance. In response to the malfunction, the tag may transmit a distress signal or, alternatively, the system may detect that the tag has malfunctioned in response to the tag no longer providing location information. Detection of this malfunction may prompt a technician to replace the malfunctioning tag with a replacement tag 508. FIG. 5D illustrates the replacement tag 508 replacing the malfunctioning tag 506. When a tag is replaced in this manner, it may be necessary to activate the replacement tag and register the replacement tag with the player. Activation of the replacement tag may be performed during or prior to the replacement operation. For example, a technician may send an activation signal to the replacement tag using a DartWandTM at the time the tag is replaced in the player's equipment.

However, in order to enable proper tracking of the participant using the replacement tag 508, the replacement tag 508 must be associated with the participant somehow, such as by adding an identifier for the tag to the participant in the registration database, adding the participant's information to an entry for the tag in the registration database, or some combination thereof. Although registration may be performed manually at the time of replacement (e.g., by a user scanning the tag and manually selecting a participant from a menu), example embodiments advantageously provide for streamlined registration with a participant. As explained earlier, relative position of the tag to the participant or to another tag associated with the participant may be captured at the time of replacement. Example methods and processes for improved registration of tags with participants are described further below.

Example Apparatus for Performing Tag Registration

FIG. 6 shows a block diagram of components that may be included in an apparatus 600 that may facilitate registration of tags with participants in accordance with embodiments discussed herein. The apparatus 600 may comprise one or more processors, such as a processor 602, one or more memories, such as a memory 604, communication circuitry 606, and a user interface 608. The processor 602 can be, for example, a microprocessor that is configured to execute software instructions and/or other types of code portions for carrying out defined steps, some of which are discussed herein. The processor 602 may communicate internally using data bus, for example, which may be used to convey data, including program instructions, between the processor 602 and the memory 604.

The memory 604 may include one or more non-transitory storage media such as, for example, volatile and/or non-volatile memory that may be either fixed or removable. The memory 604 may be configured to store information, data, applications, instructions or the like for enabling the apparatus 600 to carry out various functions in accordance with example embodiments of the present invention. For example, the memory could be configured to buffer input data for processing by the processor 602. Additionally or alternatively, the memory could be configured to store instructions for execution by the processor 602. The memory 604 can be considered primary memory and be included in, for example, RAM or other forms of volatile storage which retain its contents only during operation, and/or the memory 604 may be included in non-volatile storage, such as ROM, EPROM, EEPROM, FLASH, or other types of storage that retain the memory contents independent of the power state of the apparatus 600. The memory 604 could also be included in a secondary storage device, such as external disk storage, that stores large amounts of data. In some embodiments, the disk storage may communicate with the processor 602 using an input/output component via a data bus or other routing component. The secondary memory may include a hard disk, compact disk, DVD, memory card, or any other type of mass storage type known to those skilled in the art.

In some embodiments, the processor 602 may be configured to communicate with external communication networks and devices using the communications circuitry 606, and may use a variety of interfaces such as data communication oriented protocols, including X.25, ISDN, DSL, among others. The communications circuitry 606 may also incorporate a modem for interfacing and communicating with a standard telephone line, an Ethernet interface, cable system, and/or any other type of communications system. Additionally, the processor 602 may communicate via a wireless interface that is operatively connected to the communications circuitry 606 for communicating wirelessly with other devices, using for example, one of the IEEE 802.11 protocols, 802.15 protocol (including Bluetooth, ZigBee, and others), a cellular protocol (Advanced Mobile Phone Service or "AMPS"), Personal Communication Services (PCS), or a standard 3G wireless telecommunications protocol, such as CDMA2000 1x EV-DO, GPRS, W-CDMA, LTE, and/or any other protocol.

The apparatus 600 may include a user interface 608 that may, in turn, be in communication with the processor 602 to provide output to the user and to receive input. For example, the user interface may include a display and, in some embodiments, may also include a keyboard, a mouse, a joystick, a touch screen, touch areas, soft keys, a microphone, a speaker, or other input/output mechanisms. The processor may comprise user interface circuitry configured to control at least some functions of one or more user interface elements such as a display and, in some embodiments, a speaker, ringer, microphone and/or the like. The processor and/or user interface circuitry comprising the processor may be configured to control one or more functions of one or more user interface elements through computer program instructions (e.g., software and/or firmware) stored on a memory accessible to the processor (e.g., the memory 604, and/or the like).

Example Processes for Registering Tags with Participants

FIGS. 7, 8, 9, and 10 illustrate example flowcharts of the operations performed by an apparatus, such as apparatus 600 of FIG. 6, in accordance with example embodiments of the present invention. FIGS. 7-10 illustrate processes for using the status of one or more registered tags to perform a registration of an unregistered tag. This registration process may include identifying a participant for association with the unregistered tag based on the status information. In some embodiments, unregistered tags may be detected and identified via a display or other user interface. For example, tags may be displayed at certain positions on an interface corresponding to their position on a playing field, and unregistered tags may be marked or highlighted such that a user can select an unregistered tag and identify a participant for registration with the tag. In additional embodiments, a list of all participants may be compared against those with a registered tag, and participants associated with a registered tag may be removed from the list. Covariance pairs for the remaining participants may be created with the unregistered tag. The covariance pairs may be analyzed according to certain rules based on expected participant behavior. For example, in a football game, players typically return to a "huddle" between plays to plan out the next play. An unregistered tag that is located closer to a group of tags associated with players of a particular team between plays may be identified as likely to belong to that team, reflecting the unregistered player returning to the team huddle. This information may be cross-referenced with a list of players without registered tags to identify which players are on the same team as the "huddled" unregistered tag, but not on the list of registered players. Some example embodiments for performing tag registration that may be used in conjunction with, in addition to, or as an alternative to the example embodiments described herein may further utilize additional sensors (e.g., video cameras, biometric sensors, or the like) or physical choke points to perform registration and activation of tags. Some of these example embodiments are described with reference to copending U.S. patent application Ser. No. 14/296,703 which is herein incorporated by reference in its entirety.

It will be understood that each block of the flowcharts, and combinations of blocks in the flowcharts, may be implemented by various means, such as hardware, firmware, one or more processors, circuitry and/or other devices associated with execution of software including one or more computer program instructions. For example, one or more of the procedures described above may be embodied by computer program instructions. In this regard, the computer program instructions which embody the procedures described above may be stored by a memory 604 executed by a processor 602. As will be appreciated, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s). As such, the operations of FIGS. 7-10 when executed, convert a computer or processing circuitry into a particular machine configured to perform an example embodiment of the present invention. Accordingly, the operations of FIGS. 7-10 define an algorithm for configuring a computer or processor, to perform an example embodiment. In some cases, a general purpose computer may be provided with an instance of the processor which performs the algorithm of FIGS. 7-10 to transform the general purpose computer into a particular machine configured to perform an example embodiment.

FIG. 7 illustrates a process 700 for associating an unregistered tag with a participant using status information received from one or more registered tags. In this manner, the process 700 advantageously provides efficient registration of unregistered tags in a programmatic manner, thus reducing the complexity of a tag replacement operation in minimizing the impact upon the participant receiving the unregistered tag. Although the process 700 may be generally described with respect to a tag replacement operation (e.g., replacing a malfunctioning tag), it should also be appreciated that such techniques could also be employed during initial registration with a participant. For example, rather than manually registering each tag associated with a participant, a technician or user may register a minimum "critical mass" of tags. This registered critical mass may allow for inferences to be made about unregistered tags. For example, each player on a team may be associated with only one registered tag, even though each player is associated with four tags. The remaining three tags for each player may be identified and registered based on the location, motion vectors, or the like with respect to the one registered tag. Various other numbers of tags may be initially registered, and as more tags are manually registered, it may become increasingly likely that additional tags can be automatically registered.

At action 702, one or more tags are registered with a particular participant. For example, as described above, several tags may be initially registered with a particular participant prior to an event. However, during an event, one or more tags may experience failures or malfunctions due to physical damage to the tag, draining of a tag power source, or the like. When a tag malfunctions in this manner, a system tracking the tag may note that the system is no longer obtaining tag derived data, or, that the tag is sending a distress signal, or that a sensor has determined the tag has malfunctioned, or that tag location data is outside expected parameters, or any other known technique for detecting a tag malfunction. The malfunctioning tag may then be replaced by a technician, user, or participant. For example, a technician may swap out a malfunctioning tag in a player's shoulder pad for a functional one, or a player may be assigned a replacement set of shoulder pads. In some cases, the replacement operation may include sending a deactivation signal to the tag to be replaced, such as by using a close range deactivation signal when removing the defective tag from the participant, such as by sending such a signal from a DartWand device.

At action 704, the unregistered tag (e.g., a tag replacing a malfunctioning tag) is identified. The unregistered tag may be identified by an RTLS system when the unregistered tag is activated. For example, an RTLS system may detect that a new tag has begun broadcasting information, but that the new tag is not registered to a particular participant. The information broadcast by the new tag may include information sufficient to identify the tag to the RTLS system, and to determine that the tag is unregistered, such, for example, as a unique identifier associated with the tag, a tag model number, a tag configuration (e.g., a frequency or blink rate setting), or the like. It should be readily appreciated that in some embodiments, the unregistered tag may have previously been registered with another participant. Embodiments may function to identify these past associations and to de-register a previously registered tag in some circumstances. For example, if a particular player has more tags registered to the player than a model indicates the player should (e.g., 5 tags associated with a particular player, when players are only supposed to have 4 tags), then the system may remove the registration entry for one of the tags. Removal of the registration for a particular tag may be performed based on various factors that are used to determine which tag is improperly associated with the player. For example, if a player is associated with 5 tags and one tag is not proximate to the other four tags, then the non-proximate tag may be deregistered.

At action 706, the status of one or more registered tags is determined. The status of the registered tags may include various factors, such as the registration time (or elapsed time since registration) of the registered tag, the location of the registered tag at the time of registration, the velocity of the registered tags, with which participant the registered tags are registered, the number of registered tags associated with each participant, a unique identifier for the tag, the tag mounting location (e.g., left shoulder or right shoulder), or the like. Additional information may be derived from the tag status information, such as the identity of the associated participant, by identifying a pairing between the participant and the tag identifier using a registration database, such as described above with respect to FIG. 4.

At action 708, a participant is determined for the unregistered tag based on the information received from the registered tags. For example, the participant may be determined based on the location of the unregistered tag in relation to the registered tags, based on a motion vector for the unregistered tag in relation to the registered tags, based on other sensor data (e.g., video, audio, or biometric data) derived based on the location of the registered tags, or the like. Some example operations for determining the participant for association with the unregistered tag are described further below with respect to FIGS. 8-10. It should also be appreciated that embodiments might also determine other factors about the unregistered tag, such as with which tag (e.g., left shoulder, right shoulder, left knee, right knee) assignment of the particular participant the unregistered tag corresponds based on the status information provided by the registered tags.

At action 710, the unregistered tag is registered with the participant determined at action 708. For example, an entry in a database corresponding to the participant may be updated with the tag identifier of the previously unregistered tag, an entry in a database corresponding to the previously unregistered tag may be updated with an identity for the participant, or the like. Once the tag is registered in this manner, it may be employed for various location detection and performance analytics operations as described above with respect to FIG. 1.

FIG. 8 illustrates a process 800 for determining the identity of a participant for an unregistered tag using motion vectors. As described above, the location of tags may be monitored over time to determine the speed and direction of the motion of the participant. Aspects of the process 800 allow for identification of unregistered tags that correspond to motion vectors of other tags already registered to participants to determine participants that share the same motion vector. Participants with the same motion vector as an unregistered tag may be identified as likely participants for association with the unregistered tag.

At action 802, tag location are monitored, such as described above with respect to FIG. 1. The location of both registered and unregistered tags may be determined as part of this monitoring process. At action 804, a motion vector is determined for a particular participant based on the motion of the tags associated with the participant. For example, the distance between locations occupied by the participant at particular times may be divided by the elapsed time between the measurements to obtain an estimate of the participant's speed, and the direction of the vector may be determined by drawing a line between the locations. In some embodiments, the vector may be measured over several location measurements to ensure accuracy and to verify the location readings. Example methods, processes, and devices for determining a motion vector that may be utilized in conjunction with the techniques described herein are described further with respect to U.S. Patent Application 61/895,548 which is herein incorporated by reference in its entirety.

At action 806, an unregistered tag with the same or a similar motion vector as the participant is identified. At action 808, the participant with the similar motion vector as the unregistered tag is identified for registration with the unregistered tag. It should be appreciated that while the instant example describes the use of a motion vector to identify the participant, other factors may also be employed in conjunction with motion vector analysis to improve the participant determination process. For example, motion vector analysis may only be performed for registered tags within a certain proximity to the unregistered tag. Any method for assessing the similarity of motion of two tags may be used. For instance, tags A-W may each have 20 measurements of tag derived data, e.g. 20 observations of tag location, 19 observations of tag velocity, 20 observations of arrival times of blink data at a receiver, or other time varying measurements. Based on this data, a pairwise covariance may be determined by the formula $S_{x,y}=1/(n-1) \sum[(x_i-x_{mean})(y_i-y_{mean})]$ for each pair of tags x,y The 23 tags A-W would thus have 253 covariance pairs. If registered tag A and unregistered tag G were above a threshold value (like 0.98) they could be associated with the same participant. The threshold value could be calculated as the average of all pairwise covariances (e.g. AB, AD, and BD) associated with a particular participant (with registered tags A, B, and D). In one embodiment the threshold value could be assigned a specific value, such as 0.98. In another embodiment the threshold value could be highest pairwise covariance of a subset of pairwise covariances based on some tag attribute, such as unregistered tags, tags worn on equipment, tags near a specific registered tag, or tags in a certain area of the monitored area.

FIG. 9 illustrates a process 900 for using tag location and a spatial model to register an unregistered tag with a particular participant. As described above with respect to motion vector analysis, the location of an unregistered tag with respect to the location of registered tags may be used to identify a participant for registration with the unregistered tag. The process 900 thus facilitates identification of the proper participant by identifying registered tags proximate to the unregistered tag and determining whether the unregistered tag conforms to a spatial model for a particular participant.

As described above with respect to FIG. 4, participants may be associated with a particular model that defines the number and location of particular tags when associated with that participant. For example, a player may be associated with a certain number of tags, a referee a different number, a ball another number, and the like. Each type of participant may also have tag spatial locations defined, such that certain tags are expected to be in certain locations relative to one another. In some embodiments, different players may be associated with different models based on the player's height, wing span, assigned equipment (e.g., flak jacket) and the like. These spatial models may be employed to determine the proper participant for an unregistered tag by the process 900.

At action 902, the location of one or more tags is monitored. As above, the location of both registered and unregistered tags may be monitored. At action 904, the location of unregistered tags may be determined with respect to registered tags. At action 906, the location of the unregistered tags may be compared with one or more participant spatial models. At action 908, the spatial models may be used to identify the appropriate participant for the unregistered tag based on the location. In this manner, the use of spatial models may improve upon tag registration operations by providing another method to disambiguate between multiple unregistered tags. For example, if two malfunctioning tags are replaced simultaneously for two different players, the system may not know which tag to assign to which player. By examining a spatial model for each player and determining the location of the registered tags for those players and the location of the unregistered tags in relation to the registered tags, the process 900 may be able to assign the unregistered tags by identifying the tags that properly match each player's spatial model.

FIG. 10 illustrates a process 1000 for using known tag registrations to infer the proper participant for registration with an unregistered tag. As described above, participants may have a certain number of tags that are expected to be registered with each participant. By monitoring which participants have less than an expected number of registered tags, a RTLS system may infer which unregistered tags should be registered with each participant. In this manner, tags may be associated with a particular participant by a process of elimination through examining a list of participants who are associated with tags and tags that are associated with participants. The process 1000 may also provide for validation of registrations.

At action 1002, tag registration statuses for one or more tags are determined. The tag registration statuses may correspond to tags within a particular area (e.g., within a field of play). The tag registration statuses may inform the RTLS system of whether each tag within the particular area is registered or unregistered. Examining a particular area may also advantageously improve the efficiency and accuracy of the tag registration operation. For example, a given RTLS system may disregard participants on the sideline of a sporting event for registration operations, examining only the tags on the field of play.

At action 1004, the tag registration statuses may be used to determine whether and which participants are missing tag registrations. For example, as described above, players may be expected to be registered with 4 tags. If one player is only registered with 3 tags, and one extra unregistered tag exists within the playing field, then the system may determine that the unregistered tag should be associated with the player with 3 tags.

However, at action 1006, a validation is performed for the registration of the unregistered tag. The validation may include ensuring that the registration is accurate by examining factors such as the location of the unregistered tag in relation to the other registered tags for the participant, the use of other sensor data (e.g., a video camera) to verify the participant corresponds to the unregistered tag, or the like. The registration may not be performed if the validation fails (e.g., the unregistered tag is located at the opposite end zone from the 3 tags registered with the participant).

At action 1008, the validated participant is identified for registration with the unregistered tag in response to a successful validation. It should be appreciated that if validation is unsuccessful, the registration operation may not be performed. In the event of unsuccessful validation, the process 1000 may generate a notification to a technician to investigate the error, the process may repeat to identify an alternative participant for registration, or the system may employ a backup process for identifying the participant (see, e.g., FIGS. 8-9).

Example Filtering Using Tag Association Models

FIG. 11 illustrates an example flowchart of the operations performed by an apparatus, such as apparatus 600 of FIG. 6, in accordance with example embodiments of the present invention. The process 1100 describes how tag association models may be employed to verify and validate information received from a particular location tag. As described above, tag association models may indicate the number and location of tags associated with a particular participant. This location information may include the relative location of tags with respect to one another. When tags are registered with a particular participant, data received for those tags may be validated against a tag association model for the participant according to the process 1100 described herein. In this manner, tag association models may be used to detect errors caused by signal reflections, interference, and the like and to detect malfunctioning tags. Other example embodiments for detecting erroneous location readings that may be used in addition to or in conjunction with the methods described herein are described in U.S. patent application 61/895,548 which is herein incorporated by reference in its entirety.

At action 1102, location information is received for a first tag associated with a participant. At action 1104 location information may be received for other tags associated with the participant. At action 1106, the location associated with the first tag may be compared against the location information received for the other tags by examining a tag association model associated with the particular participant with whom the tags are associated. For example, a player model may indicate four tags disposed in the areas corresponding to the player's shoulder pads and knee pads, while a ball model may indicate two tags disposed at opposite ends of a football. The tag association model may also include an expected relative location between tags, such as an expected physical distance or range of physical distances between the tags, an expected coordinate difference (e.g., ranges in X, Y, and Z directions), or the like.

At action 1108, a determination is made as to whether the location information for the first tag is in accordance with the location of the other tags by using the tag association model. For example, if three tags of a given player in located in proximity to one another and a fourth tag is located far away, and the tag association model for the player indicates the four tags should all be in close proximity, then the data from the fourth tag may be identified as suspect. If the tag locations are not in accordance with the tag association model, the method proceeds to action 1110 and discards the data received from the first tag as erroneous. The tag may also be indicated as malfunctioning in some scenarios (e.g., where erroneous data is received repeatedly), and a technician may be notified and further data received from the tag may be discarded. Alternately, if the location of the first tag is in accordance with the tag association model and the relative locations of the other tags, then the data may be confirmed or validated at action 1112.

Accordingly, blocks of the flowchart support combinations of means for performing the specified functions and combinations of operations for performing the specified functions. It will also be understood that one or more blocks of the flowcharts, and combinations of blocks in the flowchart, can be implemented by special purpose hardware-based computer systems which perform the specified functions, or combinations of special purpose hardware and computer instructions.

In some example embodiments, certain ones of the operations herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for registering an unregistered radio frequency (RF) location tag carried by a participant, the method comprising:

receiving blink data from an unregistered RF location tag;

determining a tag location based on the blink data received from the unregistered RF location tag;

directing a camera to view the tag location determined based on the blink data received from the unregistered RF location tag;

identifying a participant at the tag location using image data obtained by the camera; and registering the unregistered RF location tag with the identified participant.

2. A method as defined in claim 1, wherein the participant is a first participant, and further comprising:

identifying a second participant at the tag location using the image data obtained by the camera; and responsive to determining that each tag associated with the second participant is functional and at least one tag associated with the first participant is unaccounted for, registering the unregistered RF location tag with the first participant.

3. A method as defined in claim 1, further comprising determining that the received blink data is from the unregistered RF location tag by referencing a registration database linking tags to participants.

4. A method as defined in claim 3, wherein an entry of the registration database includes a descriptor for registered tags, wherein the descriptor indicates a portion of the participant assigned to carry the respective tag.

5. A method as defined in claim 4, wherein the descriptor includes coordinates relative to the participant while in a particular stance.

6. A method as defined in claim 4, wherein the portion of the participant is a piece of equipment worn by the participant.

7. A method as defined in claim 1, wherein the unregistered RF location tag comprises an ultra-wideband (UWB) transmitter configured to transmit time of arrival pulses.

8. An apparatus for registering an unregistered radio frequency (RF) location tag carried by a participant, the apparatus comprising a processor coupled to memory, the memory comprising instructions that, when executed by the apparatus, configure the apparatus to:

determine a tag location based on blink data received from an unregistered RF location tag;

direct a camera to view the tag location determined based on the blink data received from the unregistered RF location tag;

identify a participant at the tag location using image data obtained by the camera; and register the unregistered RF location tag with the identified participant.

9. An apparatus as defined in claim 8, wherein the participant is a first participant, and the instructions, when executed, cause the apparatus to:

identify a second participant at the tag location using the image data obtained by the camera; and responsive to determining that each tag associated with the second participant is functional and at least one tag associated with the first participant is unaccounted for, register the unregistered RF location tag with the first participant.

10. An apparatus as defined in claim 8, wherein the instructions, when executed, cause the apparatus to determine that the received blink data is from the unregistered RF location tag by referencing a registration database linking tags to participants.

11. An apparatus as defined in claim 10, wherein an entry of the registration database includes a descriptor for registered tags, wherein the descriptor indicates a portion of the participant assigned to carry the respective tag.

12. An apparatus as defined in claim 11, wherein the descriptor includes coordinates relative to the participant while in a particular stance.

13. An apparatus as defined in claim 11, wherein the portion of the participant is a piece of equipment worn by the participant.

14. An apparatus as defined in claim 8, wherein the unregistered RF location tag comprises an ultra-wideband (UWB) transmitter configured to transmit time of arrival pulses.

15. A computer program product comprising a computer readable storage device for registering an unregistered radio frequency (RF) location tag carried by a participant, the computer readable storage device including instructions that, when executed by a processor, cause a machine to:

determine a tag location based on blink data received from an unregistered RF location tag;

direct a camera to view the tag location determined based on the blink data received from the unregistered RF location tag;

identify a participant at the tag location using image data obtained by the camera; and register the unregistered RF location tag with the identified participant.

16. A computer program product as defined in claim 15, wherein the participant is a first participant, and the instructions, when executed, cause the machine to:

identify a second participant at the tag location using the image data obtained by the camera; and responsive to determining that each tag associated with the second participant is functional and at least one tag associated with the first participant is unaccounted for, register the unregistered RF location tag with the first participant.

17. A computer program product as defined in claim 15, wherein the instructions, when executed, cause the machine to determine that the received blink data is from the unregistered RF location tag by referencing a registration database linking tags to participants.

18. A computer program product as defined in claim 17, wherein an entry of the registration database includes a descriptor for registered tags, wherein the descriptor indicates a portion of the participant assigned to carry the respective tag.

19. A computer program product as defined in claim 18, wherein the descriptor includes coordinates relative to the participant while in a particular stance.

20. A computer program product as defined in claim 18, wherein the portion of the participant is a piece of equipment worn by the participant.

* * * * *